United States Patent
Morgan et al.

(10) Patent No.: US 8,623,012 B2
(45) Date of Patent: *Jan. 7, 2014

(54) ELECTROSURGICAL PLENUM

(75) Inventors: Roy E. Morgan, Alameda, CA (US); Wayne K. Auge, II, Santa Fe, NM (US)

(73) Assignee: NuOrtho Surgical, Inc., Fall River, MA (US)

( * ) Notice: Subject to any disclaimer, the term of this patent is extended or adjusted under 35 U.S.C. 154(b) by 177 days.

This patent is subject to a terminal disclaimer.

(21) Appl. No.: 12/887,475

(22) Filed: Sep. 21, 2010

(65) Prior Publication Data

US 2011/0288547 A1  Nov. 24, 2011

Related U.S. Application Data

(60) Continuation-in-part of application No. 12/580,195, filed on Oct. 15, 2009, now Pat. No. 8,591,508, which is a continuation-in-part of application No. 12/479,578, filed on Jun. 5, 2009, now Pat. No. 7,819,864, which is a division of application No. 11/847,216, filed on Aug. 29, 2007, now Pat. No. 7,549,989, which is a division of application No. 11/147,481, filed on Jun. 7, 2005, now Pat. No. 7,354,438, which is a division of application No. 10/119,671, filed on Apr. 9, 2002, now Pat. No. 6,902,564, said application No. 11/847,216 is a continuation of application No. 10/486,739, filed as application No. PCT/US02/26277 on Aug. 15, 2002, now abandoned, said application No. 12/580,195 is a continuation-in-part of application No. 11/006,079, filed on Dec. 6, 2004, now Pat. No. 7,771,422, and a continuation-in-part of application No. PCT/US03/18116, filed on Jun. 6, 2003.

(60) Provisional application No. 60/312,965, filed on Aug. 15, 2001, provisional application No. 60/387,775, filed on Jun. 10, 2002, provisional application No. 60/387,114, filed on Jun. 6, 2002.

(51) Int. Cl.
*A61B 18/14* (2006.01)

(52) U.S. Cl.
USPC ............... 606/41; 606/45; 606/48; 606/49; 606/50

(58) Field of Classification Search
USPC .................................. 606/41, 45, 48–50
See application file for complete search history.

(56) References Cited

U.S. PATENT DOCUMENTS

| | | |
|---|---|---|
| 3,903,891 A | 9/1975 | Brayshaw |
| 4,060,088 A | 11/1977 | Morrison et al. |
| 4,901,719 A | 2/1990 | Trenconsky et al. |
| 5,569,241 A | 10/1996 | Edwards |
| 5,885,277 A | 3/1999 | Korth |
| 6,383,184 B1 * | 5/2002 | Sharkey .................. 606/41 |
| 7,004,939 B2 | 2/2006 | Mackay |
| 7,438,714 B2 | 10/2008 | Phan |

(Continued)

FOREIGN PATENT DOCUMENTS

| WO | WO-03103522 | 6/2003 |
|---|---|---|
| WO | WO-2011047148 | 4/2011 |

*Primary Examiner* — Lee S Cohen
(74) *Attorney, Agent, or Firm* — Peacock Myers, P.C.; Janeen Vilven; Justin R. Jackson

(57) ABSTRACT

An electrosurgical probe having a plenum which prevents contact of the active electrode with tissue, while simultaneously allowing a fluid/interfacing agents to contact the active electrode.

17 Claims, 23 Drawing Sheets

(56) References Cited

U.S. PATENT DOCUMENTS

| | | |
|---|---|---|
| 2003/0028189 A1 | 2/2003 | Woloszko et al. |
| 2003/0036753 A1 | 2/2003 | Morgan et al. |
| 2004/0082945 A1 | 4/2004 | Clague et al. |
| 2010/0069975 A1 | 3/2010 | Auge |
| 2010/0087815 A1 | 4/2010 | Morgan et al. |
| 2011/0087308 A1 | 4/2011 | Morgan et al. |

* cited by examiner

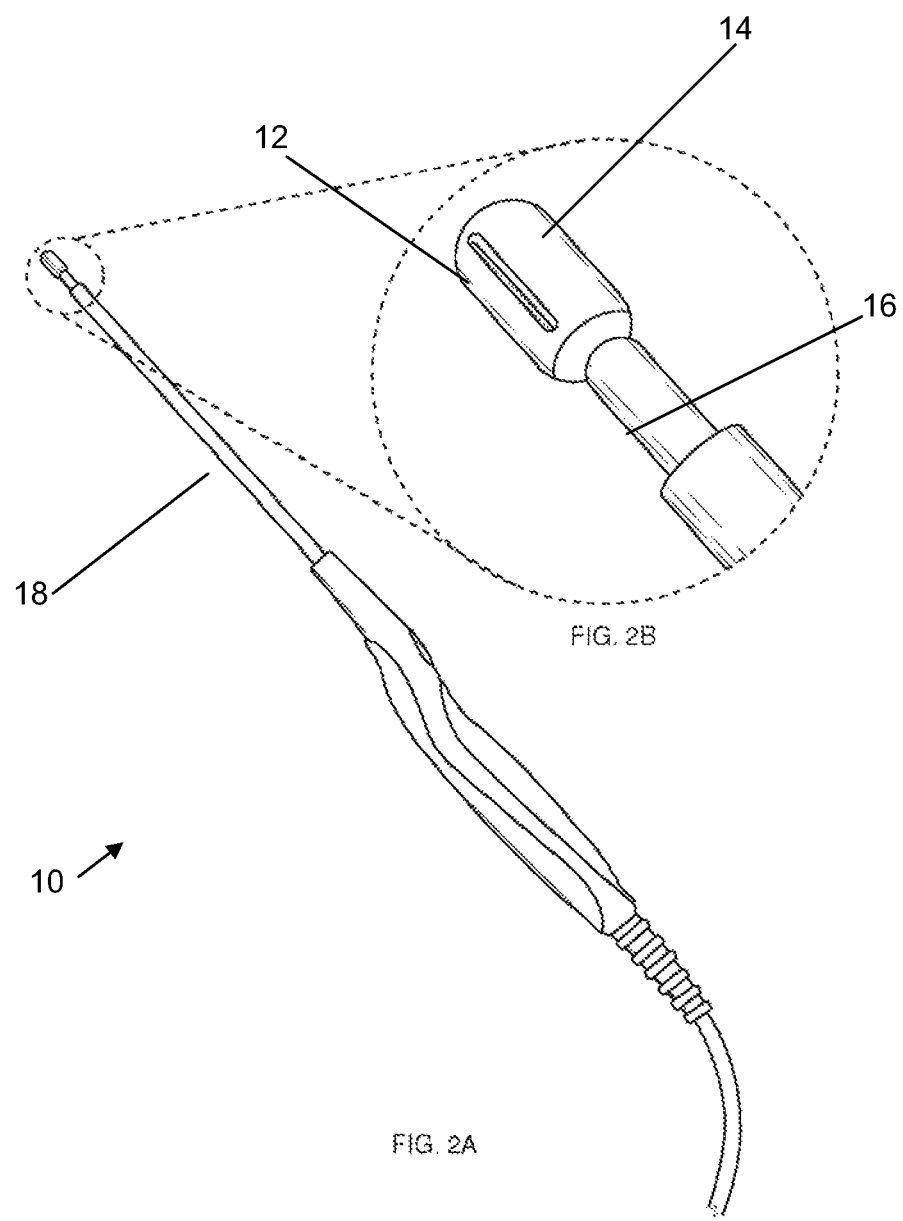

(side)

(top)

Sample Section Image of Surface Fibrillation
Original Magnification 10x

Sample Section Image Post-Treatment
Original Magnification 10x

Original Magnification 10x

ELECTROSURGICAL PLENUM

CROSS-REFERENCE TO RELATED APPLICATIONS

This application is a continuation-in-part application of U.S. patent application Ser. No. 12/580,195, entitled "Electrosurgical Plenum", filed on Oct. 15, 2009, which is a continuation-in-part application of U.S. patent application Ser. No. 12/479,578, entitled "Electrosurgery Devices", filed on Jun. 5, 2009, and issued on Oct. 26, 2010 as U.S. Pat. No. 7,819,864, which is a divisional of U.S. patent application Ser. No. 11/847,216, entitled "Electrosurgery Devices", filed on Aug. 29, 2007, and issued on Jun. 23, 2009 as U.S. Pat. No. 7,549,989, which is a divisional of U.S. patent application Ser. No. 11/147,481, entitled "Devices for Electrosurgery", filed on Jun. 7, 2005, and issued on Apr. 8, 2008 as U.S. Pat. No. 7,354,438, which is a divisional of U.S. patent application Ser. No. 10/119,671, entitled "Methods and Devices for Electrosurgery", filed on Apr. 9, 2002, and issued on Jun. 7, 2005 as U.S. Pat. No. 6,902,564, which claims priority to and the benefit of U.S. Provisional Patent Application Ser. No. 60/312,965, entitled "System and Method of Electrosurgical Biologic Tissue Modification and Treatment Utilizing Oxy-Hydro Combustion—Acid Base Shift Reactions", filed on Aug. 15, 2001, the specifications and claims of which are incorporated herein by reference.

U.S. patent application Ser. No. 11/847,216, entitled "Electrosurgery Devices", filed on Aug. 29, 2007, and issued on Jun. 23, 2009 as U.S. Pat. No. 7,549,989 is also a continuation of U.S. patent application Ser. No. 10/486,739, entitled "Methods and Devices for Electrosurgery", filed on Aug. 24, 2004, and is now abandoned, which is a National Stage Application of International Application No. PCT/US-02/26277, entitled "System and Method of Electrosurgical Biologic Tissue Modification and Treatment", filed on Aug. 15, 2002, which claims the benefit of U.S. patent application Ser. No. 10/119,671, entitled "Methods and Devices for Electrosurgery", filed on Apr. 9, 2002, and issued on Jun. 7, 2005 as U.S. Pat. No. 6,902,564, which claims priority to and the benefit of U.S. Provisional Patent Application Ser. No. 60/312,965, filed on Aug. 15, 2001, and the specifications and claims of which are incorporated herein by reference.

U.S. patent application Ser. No. 12/580,195, entitled "Electrosurgical Plenum", filed on Oct. 15, 2009 is also a continuation-in-part of U.S. patent application Ser. No. 11/006,079, entitled "Methods and Devices for Electrosurgery", filed Dec. 6, 2004, and issued on Aug. 10, 2010 as U.S. Pat. No. 7,771,422, which claims priority to and the benefit of U.S. Provisional Patent Application No. 60/387,775, entitled "Methods and Devices for Electrosurgical Electrolysis", filed on Jun. 10, 2002, and is also a continuation-in-part application of International Application No. PCT/US03/018116, entitled "Methods and Devices for Electrosurgery", filed on Jun. 6, 2003, which claims priority to and the benefit of the filing of U.S. Provisional Patent Application Ser. No. 60/387,114, entitled "Methods and Devices for Electrosurgery", filed Jun. 6, 2002, and the specifications and claims (if any) thereof are incorporated herein by reference.

BACKGROUND OF THE INVENTION

Field of the Invention (Technical Field): Embodiments of the present invention relate to the general field of electrosurgical generators that are used to power devices, such as instrument probes, and instrument probes developed for use in surgical and medical procedures.

The use of electrosurgical instruments in various types of surgical procedures has become widespread and generally consists of a system whereby a treatment device probe is connected to an electrosurgical generator. The device probe delivers the energy from the electrosurgical generator to the tissue treatment site via electrodes to provide a therapeutic effect. Device probe and electrosurgical generator architecture have been developed for particular therapeutic needs, depending upon, for example, the goals of treatment, the tissue type to be treated, and the treatment environment. Most commonly, electrosurgical generators consist of either monopolar or bipolar configurations, or both, which have become well known in the art. Likewise, either monopolar or bipolar treatment device probes have been developed to connect to those types of electrosurgical generators via a dedicated electrosurgical generator output port, either monopolar or bipolar, respectively. Active (or working) and return (reference) electrodes then function in a variety of ways based upon, for example, configuration, architecture, and connection to the electrosurgical generator. In this manner, either a monopolar or bipolar output portal, or both, exists on the electrosurgical generator into which the device probe, either a monopolar or bipolar device respectively, is connected. A monopolar device is connected to a monopolar output portal on the electrosurgical generator and, likewise, a bipolar device is connected to a bipolar output portal on the electrosurgical generator. Typically, feedback from the treatment site is then managed by way of the relevant monopolar or bipolar circuitry within the electrosurgical generator and between the device probe electrodes that are connected to the electrosurgical generator accordingly.

More generally, and to date, the electrosurgical industry has provided a wide variety of products that rely upon the importance of bulk property measurement of in situ structures/components for determining the extent and effect of electrosurgery, which has been well documented. Quantifying energy input indirectly through temperature measurement, fluid field impedance measurement, and fluid field capacitance measurement is believed to effectively correlate the degree to which electrosurgery will effect tissue and the host response thereof. Since such correlations have been extremely inconsistent in practice, a significant amount of confusion has surfaced regarding the validity and accuracy of therapeutic electrosurgical protocols, often leading to the reduction in use of electrosurgical devices for certain applications.

Historical evolution of the prior art has been to provide specific output portals for the most common types of electrosurgery; those being monopolar and bipolar. Each of these output portals is designed to provide specific controls that limit the amount of maximum current, voltage or time-based modulations of current and voltage in response to the variations in factors at the treatment site. The result is intended to control the overall output to the active (working) end of the attached device probe and keep its general state of operation within an arbitrarily selected specified "safe-range" to avoid excessive heat, current, or current density from forming within the surgical site or elsewhere within the patient at the time of treatment. Because of this prior art, the sensing devices at the tip of the probes are limited in their sensing modalities as they relate to these two modes of power output (both Monopolar and bipolar), namely temperature measurement, fluid field impedance measurement, and fluid field capacitance measurement are used to govern power delivery to the probes.

Such circuitry for this monopolar or bipolar configured output portals is contained within the physical confines of the electrosurgical generator enclosure itself, proximal to the connection of the device probe, and is coupled to an electronic and software controller that monitors said variables and continually checks their time-varying values against preset performance limits. When these performance limits are exceeded, the controlling algorithm forces a safety trip, thus modulating or shutting down the primary radio frequency-power output to the working end of the attached device. The specifics of these predefined software controlled trip points is that they are based on the electrophysical constraints electrosurgical generator manufacturers have placed on the output portals, which as previously discussed, are configuration specific (monopolar or bipolar). Thus, the physical spacing of primary components such as the active (working) and return (reference) electrodes plays a paramount role in the variation of those specific characteristics that govern said trip points for safety control. The overall industry result from this configuration model is a trajectory of "silo" thinking for each specific electrosurgical output portal, meaning that devices have been optimized for either the monopolar output portal or bipolar output portal of electrosurgical generators. Traditional thinking, based on the prior art, has been that there is no advantage in modifying the traditional physical spacing of components typically assigned to any specific output port for any specific mode, meaning that a monopolar procedure that involves a separated ground pad, typically placed at a great distance from the surgical site, has been thought to need such separation to operate effectively. Furthermore, such separation is exactly why the procedure has been named "mono" polar as the electrical poles are separated by such large relative distances that only a single pole is effectively at work within the surgical site. On the other end of the spectrum is the "bi" polar method of electrosurgery which has drawn its name from the physical basis of active (working) and return (reference) electrode proximities to one another. Thus, to date, the industry has remained ensconced in fixed paradigm of one treatment device probe configuration per output port of the electrosurgical generator; i.e. monopolar device to monopolar output port and bipolar device to bipolar output port.

U.S. Pat. Nos. 6,214,003 and 6,461,352, to Morgan, describes a fluid flow through channel that provides the ability for a fluid at the surgical site to flow through both the insulator and the electrode. In that application, the invention provides the flow through channel in the insulator and electrode because the invention seeks to remove things from the active/working electrode so that it can work better in that system. That invention therefore seeks to remove things, like bubbles so that the electrode can re-wet and continue working and effectively without obstruction, thereby enhancing visualization at the surgical site. While that invention may enhance visualization, it does not recognize the advantages of bringing all the elements within the treatment site together so that a reaction therebetween can occur.

U.S. Pat. No. 6,890,332 to Truckai, describes a fixed electrode in a recessed portion of the tip. The tip of that device, however, does not provide protection from the active electrode coming into contact with tissue at a surgical site. This is because the slight recession at the tip does not continue to provide protection from contact with the active electrode when the tip is pushed directly into the tissue. Instead, the tissue merely deforms slightly, thereby allowing the tissue to extend into the slight recession of the tip and thus make contact with the active electrode. Because the impedance value of tissue is different from that of the fluid in the surgical site, each time that the active electrode makes and breaks contact with the tissue, the impedance seen by the electrosurgical generator suddenly changes thereby making it difficult or impossible to adequately regulate the power delivered to the tip of the electrosurgical probe. Furthermore, this is why impedance, capacitance, and even to an extent temperature have been the primary parameters that have been used to control energy output from the electrosurgical generator as described above. This method of regulation of the electrosurgical energy output is extremely inaccurate when placed in a setting where tissue preservation or limited collateral damage is desired because it is often recommended that the user/physician manually induce contact of the active (working) electrode to the tissue in a non-controlled (relative to all users/physicians) manner that then continually alters the impedance, capacitance, sand temperature, the bulk properties, at the treatment site. This leads to a deficit in the ability of the user/physician to effectively control energy deposition and transfer to the treatment site in a method that preserves tissue and prevents collateral damage.

Prior art devices have addressed the problem of continually varying target tissue site impedance through increasingly complex software algorithms that monitor peak voltage outputs from the ESU using rapid circuit sensing and triggering, thereby limiting the output power as the voltage spikes to prevent excessive energy deposition to target tissue sites. These algorithms add significant complexity to ESU monitoring software algorithms and their corresponding validation. Furthermore, in many instances even with rapid peak voltage throttling by software, the total energy output from active electrodes touching tissue remains excessive to prevent significant amounts of necrosis and collateral damage as evidenced by the current literature on the topic.

Additionally, dealing with the large Voltage Standing Wave Ratios (VSWR's) created by these intermittent contacting electrode designs during electrosurgical processes often necessitates use of high-heat bearing signal generating components within the ESU (electrosurgical generator) to provide sufficient stability of the output signal against these reflections. The combined resistive, capacitive, inductive, and reflected impedance can be seen from above as accretive toward the total impedance and thereby produce much greater amounts of heat within the source (ESU). Common examples of such electrical components that must be sized to handle these types of loads include Field Effect Transistors (FET's), Operational amplifiers (Op-Amps), and inductors. The overall size of ESU's is often dictated by the requirements of heat dissipation within the console so as not to yield an excessive external skin temperature on the exterior of the housing.

Thus there is a need for device designs that protect the active (working) electrode from tissue contact and thereby stabilize the primary variables at work in causing fluctuations in load impedance at the surgical site, thus affording ESU designers greater simplicity in construction of hardware/software combinations and in some cases the complete elimination of software, such that "state-machine" electronic logic may be used which is constructed of purely hardware components that can be used to manage the lower VSWR's that are now part of protected electrode operations.

There is thus a need for an electrosurgical probe which houses the active electrode within a protected plenum that prevents contact of the active electrode with tissue, while allowing fluid at the electrosurgical site to make contact with the active electrode, and while simultaneously partially containing gasses created by the electrosurgical process such that they react with one another rather than in a manner that removes the products of electrosurgery away from the treatment site. Additionally, this plenum can then be used as a mechanical implement.

Surgical devices that deploy an electrical circuit between electrodes do so in an electrically conductive medium, which may be either in vivo biologic tissues or delivered media such as electrolyte solutions. The tissue effects produced by these devices are dependent upon the events occurring at or around the electrodes as electrical energy is converted to therapeutically useful forms. Converted energy forms can be either near-field at the electrode surface or far-field projected away from the electrodes. Near-field effects are produced by electrical current and include physiochemical events like electrothermal and electrochemical conversions; far-field effects are produced by electromagnetic radiation forces like magnetic flux densities, voltage potentials, or displacement currents generated around the electrodes. Gross electrical conduction in biological tissues is principally due to the conductivity of in situ interstitial fluids which are electrolyte water-based and thus predominantly ionic. Since the electrical charge carriers in metal electrodes are primarily electrons, the transition between electronic and ionic conduction is governed by physiochemical processes at the electrode-to-water interface within the conductive media, even though this process can be altered by electrode contact with macromolecular biologic material. Electrically conductive solutions have been used for many decades to complete surgical device circuits and no longer alone serve as a proprietary method of circuit completion. Water is the common operational media for both direct current and alternating current formulations that have been deployed in surgical device designs.

Surgical use of direct current induces tissue necrosis as a means to destroy unwanted tissue through near-field electrical current effects delivered into biologic structures. Electrolytic ablation, or tissue electrolysis, is a technique which consists of placing an anode electrode and cathode electrode at various points within or adjacent to tissue and driving direct current which typically has a range of about 40 mA to about 100 mA between them and through the biologic mass to induce tissue electrolysis. The products of tissue electrolysis kill cells by creating, in a spherical area surrounding the each electrode, local changes within tissue pH too large for cells to survive. These pH changes are created by toxic products such as chlorine, oxygen, and hydrogen ions at the anode electrode and hydrogen gas and sodium hydroxide at the cathode electrode. The region surrounding the anode becomes very acidic (~pH 2) and surrounding the cathode becomes strongly alkaline (~pH 12) with the amount of necrosis dependent upon the total electrolysis dose measured in coulombs as a product of tissue current delivery and time. A pH less than 6.0 at the anode and greater than 9.0 at the cathode reflects total cellular necrosis. Direct current applications deliver static electromagnetic fields that have inconsequential energy quanta in the region of non-necrotic tissue. Electrolytic ablation does not rely upon a thermal effect as tissue temperatures rise minimally during these procedures to levels not associated with cell death.

Surgical use of alternating current has been designed to induce therapeutic necrosis for volumetric tissue removal, coagulation, or dissection through near-field electrical current effects within biologic tissues. Radiofrequency wavelengths and frequencies do not directly stimulate nerve or muscle tissue; and, so are prevalent in medical applications. Radiofrequency surgical devices utilize tissue as the primary medium like in direct current applications; however, these surgical devices produce resistive tissue heating (ohmic or Joule heating) by an alternating current induced increase in molecular kinetic or vibrational energy to create thermal necrosis. In order to obtain the desired levels of thermal necrosis through resistive heating in a media with the exceptionally large specific heat capacity of water found in and around biologic tissues, high-levels of alternating current deposition are required to maintain heat production and conduction to remote tissue in the presence of treatment site thermal convection. In certain settings, high-level energy radiofrequency devices can be configured to produce water vapor preferentially through very rapid and intense resistive heating, overcoming the high heat of vaporization at the treatment site. Coincident with this method, the far-field time-varying electromagnetic forces of these devices deliver energy quanta able to generate charged plasma particles within the water vapor cloud. This ionizing electromagnetic radiation can induce an electron cascade, which operates over very short distances (Debye sphere) and with electron temperatures of several thousand degrees Celsius, to produce therapeutic molecular disintegration of biologic tissues as its action decays into heat. Radiofrequency thermal ablation and plasma-based techniques display use limitations associated with their design. Thermal and plasma lesions spread according to induced gradients; but, because of the variable energy transfer coefficients in the treatment settings of biologic tissues, iatrogenic tissue charring, necrosis, and collateral damage from imprecise heating or excess energy deposition can occur.

Electrolytic ablation, radiofrequency thermal ablation, and radiofrequency plasma-based surgical devices are designed for a direct electrode-to-tissue interface, concentrating near-field electrical energy to perform surgical work centered upon therapeutic necrosis. Collateral damage is a normal procedural consequence since the application locales to which these devices are deployed can often accommodate an excess or imprecise application of energy to ensure expedient procedural efficacy within varying treatment site conditions. From a surgical work energy procurement standpoint, these procedures are defined by an inefficient use of electrical energy due to the excess energy deposition that occurs within biologic tissue producing iatrogenic collateral damage. Far-field electromagnetic forces, although present, are confounded by tissue current deposition or, in the case of plasma-based radiofrequency devices, are of such a high intensity constituting local ionizing electromagnetic radiation. Electrolytic ablation, radiofrequency thermal ablation, and radiofrequency plasma devices all struggle in balancing volumetric tissue removal with healthy tissue loss because of excess collateral energy deposition into tissue.

Newer surgical uses of alternating current include non-ablation radiofrequency systems which deliver low-level energy to tissues through a protective tip architecture that prevents active electrode-to-tissue contact and therefore do not rely upon a direct electrode-to-tissue interface. The devices are deployed in a saline immersion setting with the protected electrode creating a more controlled and directed energy delivery to modify or precondition tissue allowing tissue preservation even during resection or débridement applications. Because the electrodes do not contact tissue during activation, electrical current deposition is concentrated into an interfacing media within the protective housing rather than directly into and through biologic tissue as in ablation-based devices. The protective housing provides the ability to move, manipulate, and segregate the near-field effects both tangentially and perpendicularly to the tissue surface during modification or preconditioning; and, it can serve as a mechanical implement and selective throttling vent/plenum during use. For example, the near-field effects are often configured to match current density dispersion with biologic tissue surfaces in a procedure-specific manner. This design allows more consistent electrical current near-field effects at the electrode surface because the circuit is not required to accommodate widely fluctuating impedance changes that tissue contacting electrodes create. Accordingly, tissue electrolysis and resistive (ohmic or Joule) tissue heating can be prevented. These devices allow a more efficient surgical work energy procurement as iatrogenic collateral tissue damage is minimized without compromising procedural efficacy. Non-ablation devices can deliver useable far-field electromagnetic forces to surface and subsurface tissues designed to create quantitatively and qualitatively larger strengths in tissue not damaged by excessive current deposition or ionizing electromagnetic radiation. These devices are used to permit normal tissue healing responses during modification and preconditioning through segregated near-field effects, while creating far-field electromagnetic intensities designed to induce tissue healing responses within the preserved tissue not subjected to collateral damage.

The application of radiofrequency energy upon an electrically conductive media can follow distinct pathways based upon the nature of electrical work desired. These pathways are determined by structural rearrangements of water molecules that are subjected to the radiofrequency energy effects upon the interfacing media molecular dynamics. Whether the interfacing media is in or around biologic tissues, it is governed by hydrogen bond behavior and proton transport that allow for widely malleable structural fluctuations of liquid water molecules. These fluctuations are due to water's very dynamic hydrogen bond network which displays the inherent ability to both exhibit simultaneous behavioral states and to rapidly reconfigure to accommodate physiochemical perturbations. With ablation- and plasma-based radiofrequency systems, resistive heating is produced predominantly by molecular kinetic and vibrational motions occurring within and amongst the hydrogen bond network. Rapid and intense resistive heating can produce a phase transition from liquid water to water vapor as vibrational motions further exert a predominate role in the ultrafast loss of liquid water's structural configuration leading toward phase transition. This process is energy intensive due the high specific heat capacity and heat of vaporization of water. In the presence of charged species like salts, this temperature driven phase transition process from rapid resistive heating at the electrode is slowed by 3-4 times, which further increases the amount of energy required to reach phase transition. Once phase transition occurs, water vapor can be ionized by the electromagnetic forces associated with this radiofrequency energy level required to drive the heating process to phase transition.

In contrast, non-ablation radiofrequency energy requirements are low because the requisite energy input is limited to splitting water which then creates a repetitive molecular energy conversion loop that self-fuels due to the exothermic reaction of water reconstitution. Charged species like salts, in distinction to their effect during resistive heating, decrease the system energy requirements because they serve as a energy salt-bridge catalyst facilitating water splitting by forming, breaking, and nucleating hydrogen bonds between acid-base pairs and water molecules. As this study demonstrates, water splitting is a low energy initiation process associated with non-ionizing electromagnetic forces. Without the protective housing around the active electrode, this physiochemical process would be rendered inconsequential due to the large fluid flow and convective forces present during surgical application. It is for this reason that ablation-based systems have been designed with ever increasing energy levels and associated ionizing electromagnetic radiation while non-ablation systems have focused upon limiting energy requirements by refining the energy procurement and delivery process to preserve tissue.

The near-field electrothermal effects of non-ablation radiofrequency energy are governed by the nature of electrical work performed upon the intermolecular hydrogen bonds of water-based interfacing media. Energy generation is created by a repetitive molecular energy conversion loop rather than by high energy resistive heating of water. Splitting water is a mildly endothermic reaction that is driven by the low-energy near-field effects of non-ablation current; whereas, reconstitution back to water is exothermic providing assistive energy for further repetitive molecular energy conversion loops ultimately deployed for surgical work. The alternating current allows each electrode to perform each redox half-reaction, but the effects can vary between electrodes because of architectural nuances. The initial reaction activation barrier is the four electron oxidation of water to oxygen during the anode phase of water splitting. This barrier is overcome by increased voltage potentials between the electrodes rather than by increased current so that architectural nuances of the electrodes are primarily due to the magnitude of voltage potential difference rather than current density disparities. At the frequencies employed, this process is very inefficient at producing non-soluble gas. When non-soluble gas is produced, it is limited to molecular hydrogen and oxygen which is effectively managed by the protective housing throttling vent/plenum. Water vapor is not produced demonstrating the low-level energy deployment well below water's heat of vaporization. As a corollary, excessive water vapor production during resistive heating has been shown to significantly impair visualization of the ablation treatment site.

The near-field electrochemical events of non-ablation radiofrequency energy are also governed by the nature of electrical work performed upon the water-based interfacing media. During the repetitive molecular energy conversion loop, alternating current can also facilitate an otherwise inefficient and more complex chemical reaction within the interfacing media rather than simple phase transition to water vapor as in ablation-based devices. The intermediary products and reactants of the repetitive molecular energy conversion loop may combine to create an acid-base shift desirable for therapeutic interventions through techniques such as capacitive deionization and concentration enrichment. Because of the protective housing throttling vent/plenum, these products can be delivered in a controlled and localized fashion through precipitation, sedimentation, thermal, or chemical gradient forces into the treatment site through redox magnetohydrodynamic fluid flow. Much like the electrothermal gradients, these electrochemical modification gradients can be driven toward tissue surfaces. For example, sodium hypochlorite can be precipitated preferentially based upon device design configuration to react with a wide variety of biomolecules including nucleic acids, fatty acid groups, cholesterol, and proteins at tissue surfaces. Additionally, pH shifts have been shown to produce tissue surface alterations effecting transport properties and extracellular composition. Water vapor itself is not a therapeutic product or event, limiting ablation-based devices to thermal interventions.

The far-field effects of non-ablation radiofrequency devices can manifest due to a minimal current density at or within biologic tissues, and hence magnetic field flux densities within the protective housing, and an high voltage potential force resulting in non-ionizing electromagnetic intensities designed for therapeutic use. Not only do these high voltage potentials increase the ability to perform redox reactions in conductive media by facilitating the repetitive molecular energy conversion loop, voltage potentials not coincidentally have been shown to be a principle driver of non-ionizing electromagnetic effects upon biologic tissue. Because these electromagnetic forces carry energy that can be imparted to biologic tissue with which it interacts, higher voltage potentials enable oxidization or reduction of energetically more demanding tissue constituent macromolecular compounds other than water. These forces are deployed at the protective housing-to-tissue interface, unencumbered by current deposition, typically scaled at about 0.1 to about 1.5 mm distances from the electrode, rather than processes at the electrode-to-tissue interface as in, for example, plasma-based systems where the ionizing electromagnetic radiation generates high energy thermal particles that interact with biologic tissue.

Once non-ionizing electromagnetic fields have been produced from a given charge distribution, other charged objects within the field, such as biologic tissue, will experience a force, creating a dynamic entity that causes other tissue charges and currents to move as their strengths are typically lower. When non-ionizing electromagnetic radiation is incident on biologic tissue, it may produce mild thermal and/or weaker non-thermal field effects. Complex biological consequences of these fields are exerted through such mechanisms as tissue voltage sensor domains, stress response gene expression, and direct voltage-to-force energy conversion molecular motors.

Further, Chondron density within the Superficial Zone has been shown to decrease with age, disease, injury, and in response to some interventions and may predispose articular cartilage to extracellular matrix-based failure through an inability to support the mechanotransductive demands of physiologic loading. Since chondron shape and orientation reflect inter-territorial extracellular matrix architecture, chondron density is an important descriptor for functional cartilage. Interventions that alter chondron density may provide insight into the treatment outcome of focal lesions.

Articular cartilage disease constitutes a large burden for our population which needs to be addressed with practical socioeconomic solutions. Because articular cartilage has offered surface changes as the first readily diagnosable visual and tactile cue of its degeneration, the orthopedic surgeon has been given the responsibility of first responder. This responsibility has led to the limited adoption of mechanical shavers and thermal or plasma ablation devices as a viable treatment for early articular cartilage disease due to the collateral damage and lesion progression they can cause. The opportunity to achieve successful early surgical intervention for articular cartilage lesions rather than waiting for full-thickness lesions to develop has recently been made possible with the advent of non-ablation radiofrequency technology.

Non-ablation radiofrequency technology enables the selective targeting and removal of the damaged tissue associated with early articular cartilage disease without causing necrosis in the contiguous cartilage tissue surrounding the lesion. This is accomplished by a protected electrode architecture (see FIG. 11) that prohibits electrode-to-tissue contact so that the resistive tissue heating and tissue electrolysis induced by electrical current and associated with tissue necrosis do not occur like in thermal and plasma ablation devices. The protective housing creates a primary reaction zone that is shielded from the large physical fluid-flow and convective forces present during surgical application enabling deployment of low-level radiofrequency energy to create low-energy physiochemical conversions that can be used for surgical work. A repetitive molecular energy conversion loop under non-ionizing electromagnetic forces is created wherein the rapid splitting and reconstitution of the water molecule occurs. A sister technology to the fuel cell that harnesses energy from the molecular bonds of water, these physiochemical conversions create products that are concentrated through techniques such as capacitive deionization and concentration enrichment and delivered to the treatment site in a controlled and localized fashion through precipitation, sedimentation, thermal, or chemical gradient forces via redox magnetohydrodynamic fluid flow. Thermal and plasma ablation devices have exposed electrodes making any attempt at low-energy physiochemical conversions inconsequential due to the large physical fluid-flow and convective forces present during surgical application; hence, their design necessitates a large amount of energy delivery to the treatment site that leads to collateral damage around the tissue target.

Non-ablation radiofrequency treatments are a surface-based intervention useful for surface-based conditions such as early articular cartilage damage. The low-level energy delivery is configured to modify/precondition diseased articular cartilage to a state amenable to a safe and effective gentle mechanical debridement with the protective housing leading edge. The non-ablation radiofrequency energy products effect the accessible and degenerate surface matrix structure of damaged cartilage tissue preferentially rather than the intact chondron and matrix tissue deep to the surface lesion level. In this manner, the non-ablation energy takes advantage of the altered pericellular and extracellular matrices of diseased cartilage by preparing damaged tissue for subsequent debridement with the protective housing leading edge through augmented and/or naturally facile tissue cleavage patterns. As early articular cartilage disease manifests as matrix failure, non-ablation radiofrequency technology creates a matrix-failure-based intervention that corresponds to cartilage biology.

The matrix failure of surface fibrillation remains an attractive therapeutic target for early surgical intervention modalities. By safely removing diseased surface fibrillation that serves as both a mechanical stress riser and a source of biologic load that propagate damage, these lesions can be stabilized. Lesion stabilization remains a necessary prerequisite toward articular cartilage tissue preservation since a residually healthy lesion site is an essential substrate for permitting or inducting effective healing responses. It has been demonstrated (see FIGS. 21A and B) that Superficial Zone characteristics with viable chondrocytes can be preserved during the targeted removal of surface fibrillation. Since the area adjacent to surface fibrillation often exhibits a soft character as noted by tactile cues, it would be useful if this tissue could be treated concurrent with the surface fibrillation whereby such a procedure would serve both as a therapeutic intervention for the tactile soft lesion and as a defined safety margin during the targeting of surface fibrillation lesions.

Chondron density has been shown to decrease with age, disease, injury, and in response to some interventions and may predispose articular cartilage to extracellular matrix-based failure through an inability to support the mechanotransductive demands of physiologic loading. Since chondron shape and orientation reflect inter-territorial extracellular matrix architecture, chondron density is an important descriptor for functional and degenerating cartilage. Interventions that alter chondron density through matrix modification may provide insight into the treatment outcome of focal lesions. It has previously been shown (see FIGS. 21A and B) that chondron density with live chondrocytes preferentially increases within the residual Superficial Zone after targeted removal of surface fibrillation with non-ablation radiofrequency techniques.

Aside from exploiting the mechanical cleavage patterns inherent in the Superficial Zone of early disease for lesion stabilization, theoretical matrix modification of the Superficial Zone without damage to the chondrocyte and chondron has been considered possible due to this zone's unique matrix properties. Articular chondrocytes are surrounded by a protective layer, the pericellular matrix (PCM), which is thought to function as a non-linear mechanical filter that modulates the physiochemical and biomechanical environments experienced by chondrocytes through processes like transmembrane signaling. The PCM displays distinct biomechanical properties when compared to the ECM. For example, the Young's modulus of the PCM is uniform with tissue depth in that it is similar to the ECM modulus of the Superficial Zone but significantly lower than the ECM modulus of the Transitional and Deep Zones. This disparity in properties, or stiffness ratio, allows the chondrocyte environment to be more consistent when confronted with large incongruities in local zone- and region-specific ECM forces. The PCM may protect the micromechanical environment of the chondrocyte in regions of high local strain such as in the Superficial Zone and may amplify lower magnitudes of local strain such as those occurring in the Transitional Zone. Further, the fluid permeability of PCM relative to the ECM is much lower allowing the functional phasic properties of the ECM during loading to be shielded from the chondrocyte. These unique properties would allow the chondron and chondrocyte in the Superficial Zone to accommodate alterations in the ECM with a protective PCM posture; whereas once the Transitional Zone chondron and chondrocyte are exposed to a surface-level environment due to acute damage or disease, the PCM of the Transitional Zone may amplify the increased ECM strains witnessed by the Transitional Zone's new surface locale to a detrimental level for both the chondrocyte and matrix. These PCM properties may partially explain the retention of viable chondrocytes in the Superficial Zone after non-ablation radiofrequency energy application; as well as, the significant disease progression that can be induced by mechanical shavers and thermal or plasma ablation devices that create an exposed and damaged Transitional Zone that is then subjected to repetitive physiologic loading.

BRIEF SUMMARY OF THE INVENTION

An embodiment of the present invention relates to an electrosurgical tool which has a plenum disposed at least partially around an active electrode, the plenum having one or more openings which permit fluid to enter the plenum chamber, and the plenum shielding tissue from the active electrode. The tool can also have a plurality of active electrodes and/or a plurality of openings in the plenum. An exterior surface of the plenum can be textured, which texture can be a roughened surface. Optionally, the plenum can have a shape useful for a surgical procedure, which can include a knife blade, which knife blade can optionally be serrated. In one embodiment, the openings can be on an end-portion of the plenum. The plenum can have at least one elongated opening orientated along its primary axis, or a plurality of elongated openings orientated along its primary axis. In one embodiment, the active electrode itself does not have any openings, flow-through channels, portals, and/or windows.

An embodiment of the present invention also relates to a method for performing an electrosurgical procedure which includes providing an electrosurgical apparatus having active and return electrodes; and disposing a plenum around the active electrode, the plenum comprising one or more openings which permit entry of fluid while preventing anatomically-specific tissue structures from contacting the active electrode. The anatomically-specific tissue can be targeted tissue and/or in-tact tissue. Optionally, the openings of the plenum can be disposed along a primary axis of the plenum. In the method, at least a portion of the plenum can extend beyond at least a tip of the active electrode. In one embodiment, the plenum does not comprise merely a recessed electrode.

An embodiment of the present invention relates to an electrosurgical tool having a plenum disposed at least partially around an active electrode, the plenum having a plurality of openings which permit fluid to enter the plenum chamber. The openings in the plenum can be small enough to inhibit and/or prevent the ability of intact tissue from entering the plenum.

An embodiment of the present invention also relates to an electrosurgical tool having a plenum disposed at least partially around an active electrode, the plenum having one or more openings which permit fluid to enter the plenum chamber, the openings being less than about 100% of any side of the plenum. Optionally, the openings can be less than about 80%, 70% 50%, or 35% of any side of the plenum.

An embodiment of the present invention also relates to an electrosurgical tool having a plenum disposed at least partially around an active electrode, the plenum having one or more openings which permit fluid to enter a chamber of the plenum, the plenum not entirely open on a tip thereof. The openings can be small enough to inhibit the ability of intact tissue from entering the plenum. The openings can be small enough to prevent intact tissue from entering the plenum.

An embodiment of the present invention also relates to an electrosurgical tool having an electrode surrounded on all sides by a plenum surface, the plenum surface having one or more openings which provide fluid flow and communication of a fluid past the active electrode. In one embodiment, the shape, size, and/or location of the one or more openings can be selected such that the fluid travels past the active electrode at a predetermined velocity.

Aspects, advantages and novel features, and further scope of applicability of embodiments of the present invention will be set forth in part in the detailed description to follow, taken in conjunction with the accompanying drawings, and in part will become apparent to those aspects and advantages of embodiments of the present invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIGS. 2A and B are drawings which illustrate an embodiment of the present invention whereby the electrosurgical device has a plenum disposed on its tip which prevents the active electrode from contacting tissue during an electrosurgical procedure and allows all the elements of electrosurgery to inter mingle or be brought to the active (working) electrode;

FIG. 5 is a partially exploded view drawing which illustrates a plenum that can be placed about a plurality of active electrodes;

DETAILED DESCRIPTION OF THE INVENTION

In one embodiment, the present invention allows the general field of electrosurgery to use electrosurgical generators to power devices, such as instrument probes, developed for use in surgical and medical procedures.

As used throughout the specification and claims of this application, the term "plenum" is given a broad meaning and is intended to mean any type of a cage, guard, protective structure, or other device, system, method, apparatus, capable of at least partially housing an active electrode and inhibiting the ability for the active electrode to come into contact with a portion of tissue which is outside of the plenum. The term "plenum" also includes a device, method or apparatus that regulates the media and products by providing a mechanism for mechanically restricting the inflow of fluid and the outflow of the endogenously produced gases during electrosurgery at or about the active (working) electrode(s). The term "plenum" does not mean a mere slightly concave structure which permits tissue to come into contact with the active electrode when the tissue is pressed against the plenum.

Figure 1:
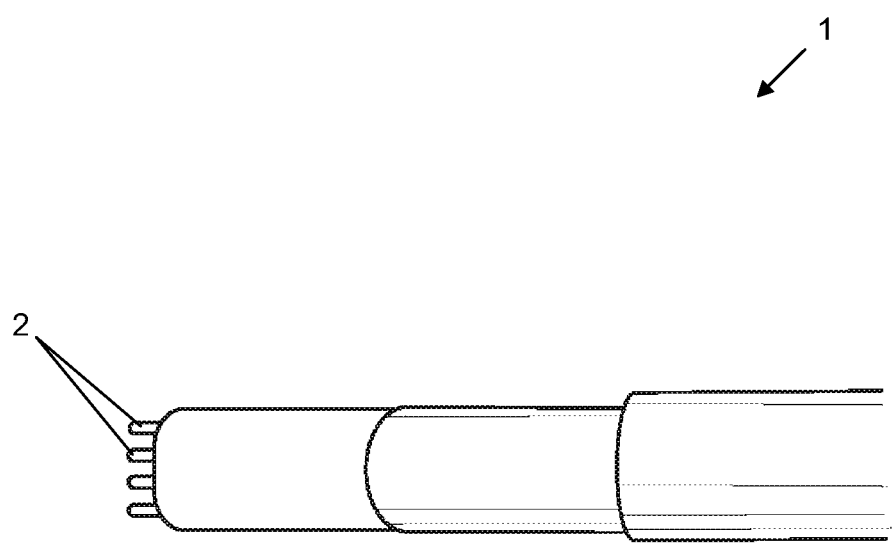
FIG. 1 is a drawing which illustrates the prior art traditional method of delivering high frequency electrical current to the human body during a treatment procedure.

As illustrated in FIG. 1 prior art electrosurgical devices 1 typically comprise one or more exposed active electrodes 2 which project from an end thereof. In typical electrosurgical applications, the surgical site is submerged in a conductive saline solution. The high frequency electric current flowing through the active electrodes and into the patient thus encounters differing amounts of impedance dependent upon whether the probe is contacting tissue of the patient or only the interfacing media. Accordingly, differing amounts of power are provided to the surgical site as the active electrodes 2 come in and out of contact with tissue of the patient.

As illustrated in FIGS. 2A, and B, the present invention comprises electrosurgical probe 10 having active electrode 12 housed within insulating plenum 14. Desirable results can be obtained when probe 10 is operated in a monopolar mode or a bipolar mode. When operated in a bi-polar mode, return electrode 16 is optionally disposed slightly proximal along lumen 18 from insulating plenum 14. In an alternative embodiment, an active and reference electrodes can optionally be disposed within insulating plenum 14. In yet another embodiment active electrode 12 can be housed within plenum 14 and plenum 14 can optionally be formed from a conductive material and used as a return electrode or as a portion of the return electrode.

In a preferred embodiment, insulating plenum 14 is made from a non-conductive material which most preferably comprises a glass, ceramic, or other material which can withstand high electric voltage and high temperatures whereby the plenum is a mechanical implement used to assist or for treatment.

Figure 3A:
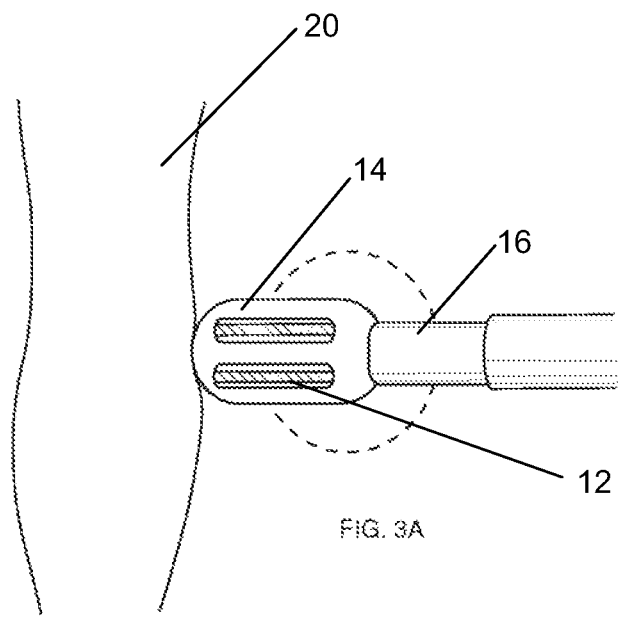
FIGS. 3A and 3B are drawings which respectively illustrate an embodiment of the present invention and a prior art device pressed against tissue and the theoretical current flow lines from the active electrodes to the return electrodes therefrom.
Figure 3B:
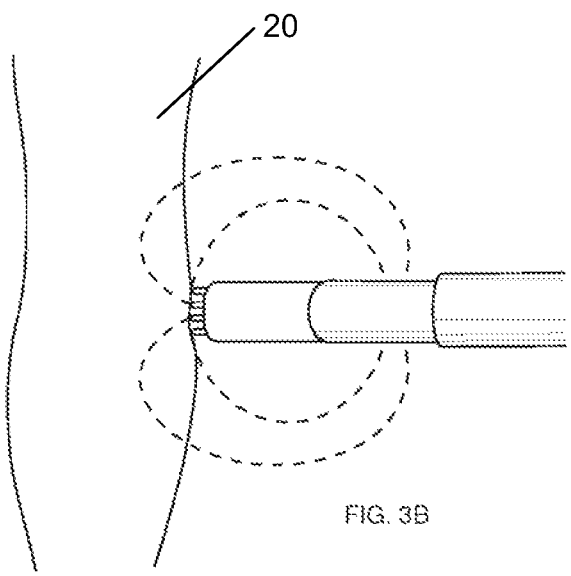

As illustrated in FIGS. 3A and 3B, which respectively illustrate the probe of the present invention and a prior art probe each contacting tissue 20 at a surgical site. The dashed lines illustrate current flow paths from the active electrodes to the return electrode. As can be seen in the drawing, the current flow paths, and thus impedance, is much more constant and predictable with the probe of the present invention since only the fluid at the surgical site acts as the conductor between the active and return electrodes, whereas the tissue also acts to conduct the flow of electricity with the prior art device, particularly when the active electrode is in contact therewith. Not only does the present invention thus permit a more constant and predictable amount of power to be delivered to a surgical site, and thus more predictable surgical results, but the present invention also greatly reduces the potential for significant current flow through the tissue, such current flow can cause damage to the tissue, thus making the present invention a safer surgical tool than the devices of the prior art. Furthermore, the shape of the electrode can then be optimized for its electrical properties rather than for tissue interfacing properties which all prior art exemplifies. For example, a sharpened edge of the active (working) electrode provides for beneficial electrical properties in a conductive or electrolyzable environment by optimizing current density at the solid (electrode)/fluid (interfacing media) contact points as opposed to within the tissue as all prior art exemplifies.

Figures 4A, 4B, 4C:
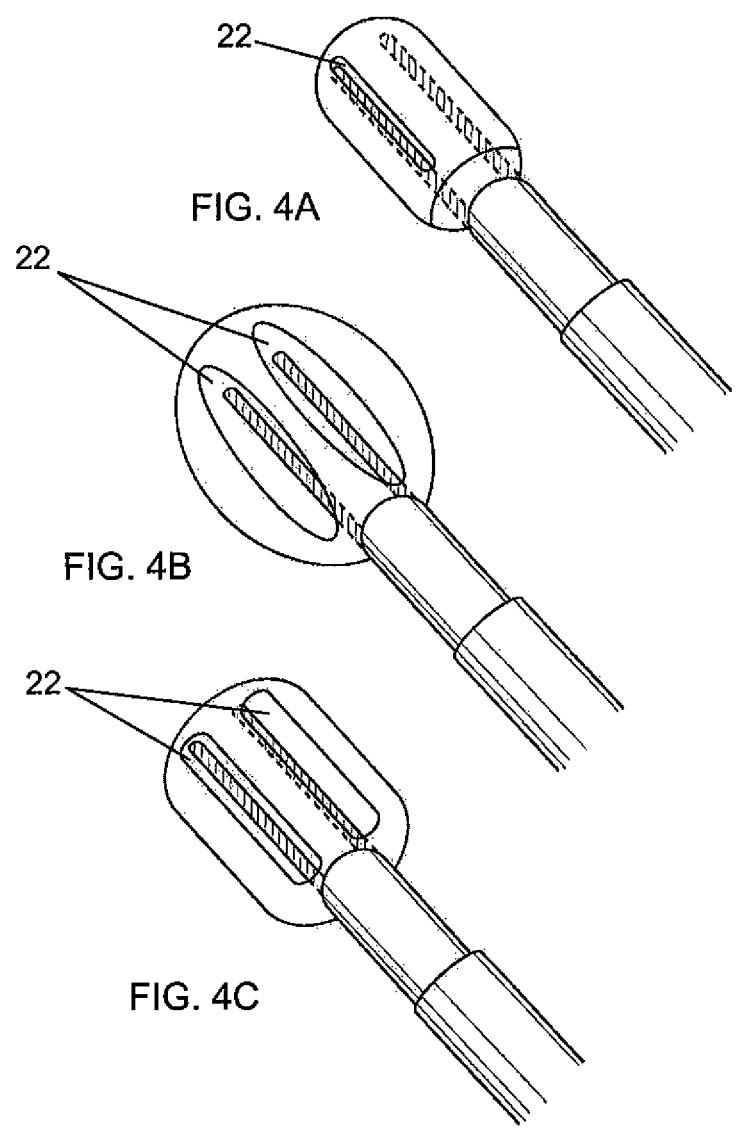
FIGS. 4A-C are drawings which illustrate alternative plenum configurations according to an embodiment of the present invention.
Figure 6:
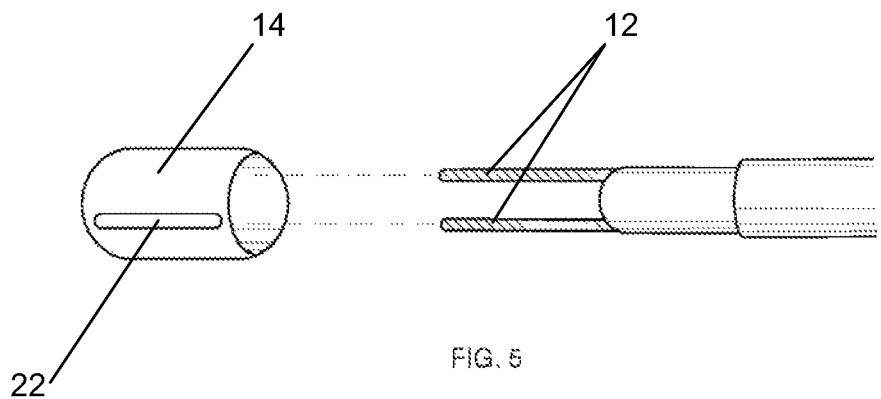
FIGS. 6A-D illustrate different configurations of a plenum according to an embodiment of the present invention.
Figure 6A:
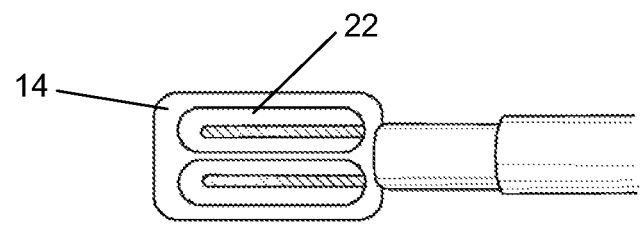
Figure 6B:
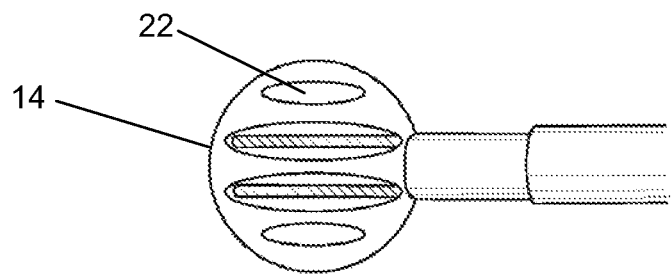
Figure 6C:
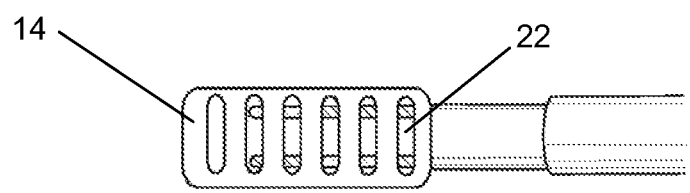
Figure 6D:
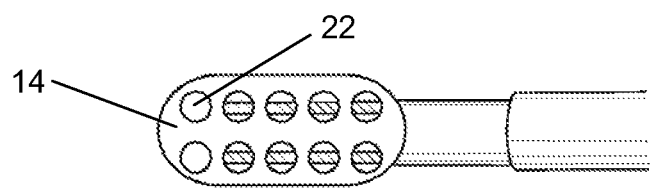

Referring now to FIGS. 4A-5, in one embodiment, a plurality of active electrodes 12 can optionally be disposed within plenum 14. One or more openings 22 are preferably provided in plenum 14 such that fluid at the surgical site can enter and exit the plenum chamber (i.e. the inner area of plenum 14), while tissue is excluded from the inner area of plenum 12. FIG. 5 illustrates a partially exploded view such that the plurality of active electrodes 12 are exposed.

FIGS. 6A-D illustrate a few of the possible configurations of plenum 14 and openings 22. Neither the particular shape of plenum 14 nor the shape, size, location or number of openings 22 are essential to the present invention. Upon studying this application, those skilled in the art will readily appreciate that desirable results can be obtained from multiple shapes, types and sizes of plenum 14 and openings 22. Furthermore, the plenum can be used as a mechanical implement that aids the user/physician during treatment.

Figure 7A:
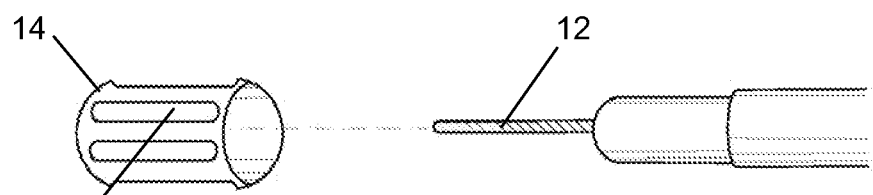
FIGS. 7A and B are partially exploded view drawings which illustrate a plenum that can be placed about a single active electrode which single active electrode can respectively be thin or thick.
Figure 7B:
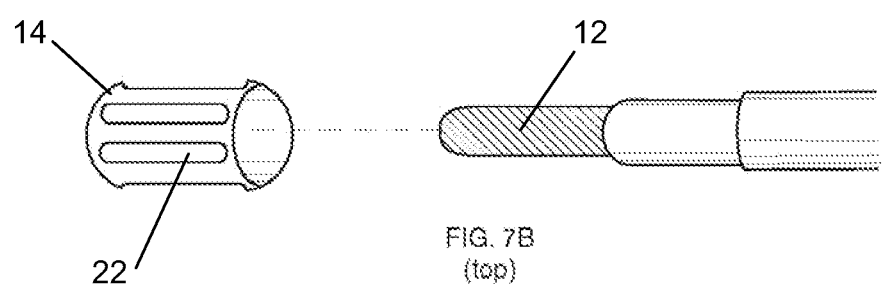

FIGS. 7A and 7B respectively illustrate partially exploded side and top views of an embodiment of the present invention wherein a single active electrode 12 is provided, which active electrode comprises a thin and wide shape.

Figure 8A:
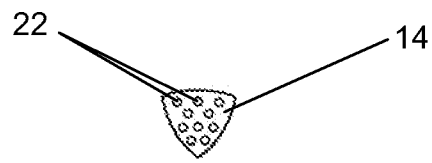
FIGS. 8A and B are side and end view drawings which illustrate an embodiment of the present invention wherein the plenum comprises a knife blade with a plurality of openings disposed on an end thereof.
Figure 8B:
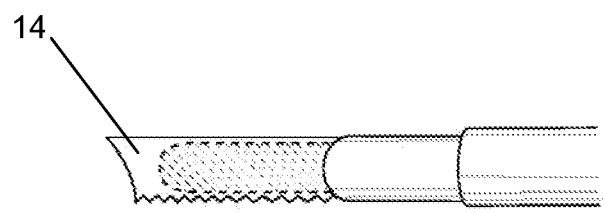
Figure 9:
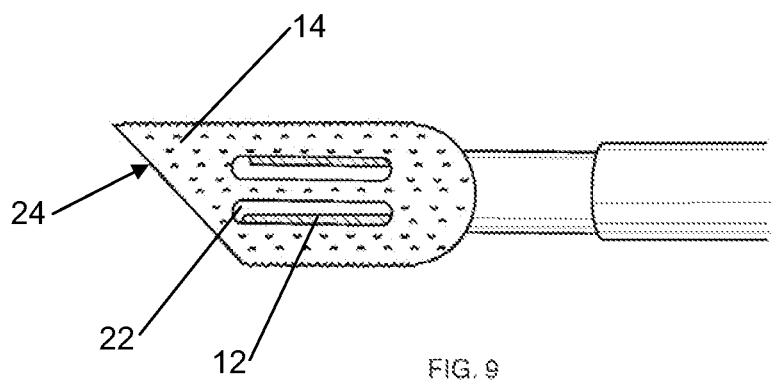
FIG. 9 is a side-view drawing which illustrates an embodiment of the present invention wherein the plenum comprises a knife end, a plurality of side openings, and roughened surface.

FIGS. 8A and 8B are drawings which respectively illustrate end and side views of an embodiment of the present invention. As can be seen, plenum 14 can have a shape, texture, and/or design which provide additional benefits during a surgical procedure. As illustrated in those figs, plenum 14 comprises a knife-blade shape which permits a surgeon to simultaneously make physical cuts during an electrosurgical procedure. A knife-blade shape, which can be serrated, is particularly effective if the plenum is made from a hard material, such as a ceramic. In this embodiment, openings 22 are placed at the tip of plenum 14, however one or more holes can optionally be disposed in a different location. Other shapes and textures of plenum 14 can also be desirable. FIG. 9 illustrates but one such shape and texture. As illustrated therein, plenum 14 preferably comprises a textured or roughened surface, for example a rasp-type surface, which can be useful for filing and/or grinding during an electrosurgical procedure. In addition to a textured surface, plenum 14 can also optionally comprise an additional useful shape, such as blade 24. The plenum can serve as a stabilizing platform for the device against the tissue surface. This provides tactile feedback to the user/physician during treatment. Accordingly, any useful configuration can be created by those skilled in the art, such as but not limited to ball tip, flat tip, needle tip, rubber tip (as in a composite plenum), curette tip, mellonbailer tip, potato-peeler like tip, and the like. Composite material plenums are particularly useful to add an additional feature for the user to gain information from the treatment site at the tip of the probe.

Figure 11:
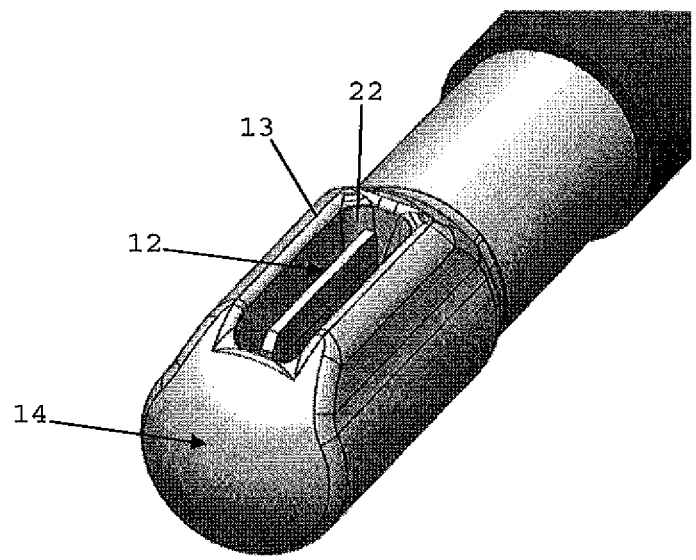
FIG. 11 illustrates a radiofrequency device tip according to an embodiment of the present invention with a protected active electrode designed for non-ablation surgical treatments in a saline immersion setting.

FIG. 11 illustrates just such a composite plenum wherein an elastomeric lip 13 is disposed along the edge of Plenum 14 opening 22. Elastomeric lip 13 provides the ability to engender variable force tactile feedback to the user as compression is made up against tissue surfaces. The location of and dimensions of such elastomeric composite features are not limited to the specifics shown in FIG. 11, but are representative of a composite feature set of the plenum entry or plenum exterior that enhance tactile feedback intraoperatively to the user. Such composite system combinations of semi-rigid elastomers and rigid insulating materials form a basis for a translating electrode/plenum assembly that is controlled by the force with which the user applies to compress it against the target tissue site.

Figure 10A:
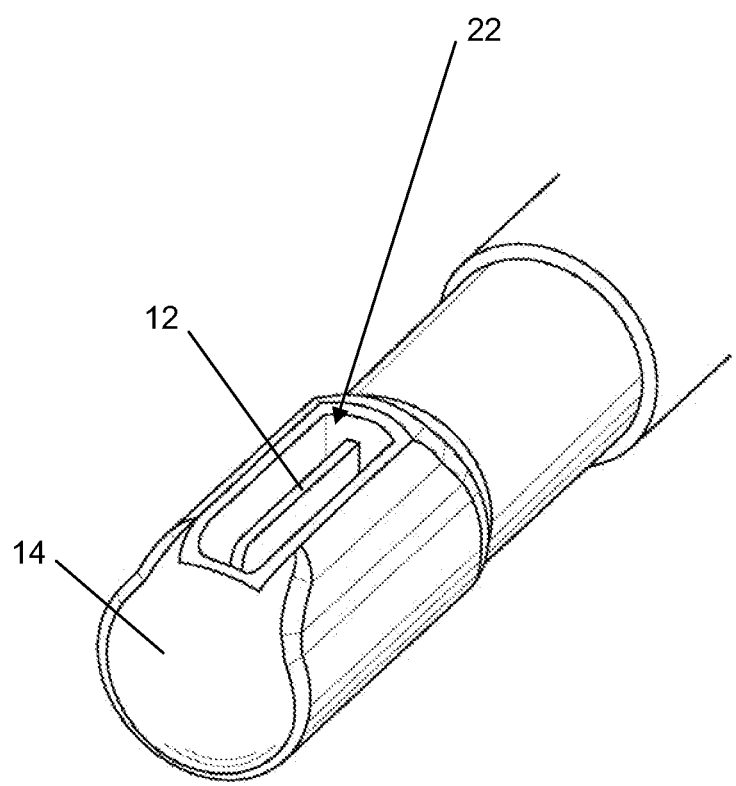
FIGS. 10A and B illustrate an embodiments of the present invention wherein the plenum is respectively dull and sharp around the opening therein.
Figure 10B:
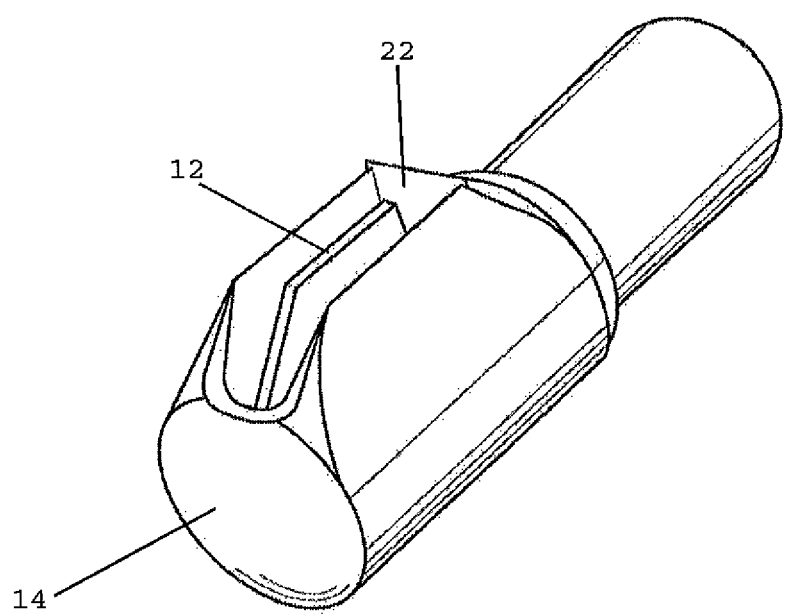

FIG. 10A illustrates an embodiment wherein the portions of plenum 14 surrounding opening 22 are dull. FIG. 10B illustrates an embodiment of the present invention wherein plenum 14 is sharp around opening 22 thereby providing a surgeon with a physical cutting apparatus while simultaneously providing an electrosurgical apparatus.

In one embodiment, the opening in the plenum is preferably dimensioned for specific procedures to protect tissue of the most common anatomical dimension expected to be encountered in the specific procedure from entering the plenum.

Embodiments of the present invention preferably provide the reduction and/or elimination of excessive field-effect transistor, OP-Amp, and/or inductor usage in the construction of primary radio frequency ("RF") delivery circuitry within electrosurgical console unit ("ESU"). The outcome of voltage standing wave ratio stabilization is less heat production within the ESU and the reduction in size of the ESU. Where probe designs hold total impedance to $100\Omega$ or less, console sizes can preferably be reduced by as much as 50%-75% in size. This provides a mechanism by which ESU's can be designed to fit ever-increasing limits in space and space competition within the operating room for consoles specific to various procedures. Further, as the size decreases, it may be housed within the hand piece of the device itself make the electrosurgical probe cordless, with a self-contained power source and circuitry.

More specifically, in one embodiment, the present invention relates to specific methods of connection of such devices to electrosurgical generators that provide active enhancement of output signal monitoring. Embodiments of the present invention also relate to specific management of circuit characterization when a single mode output from an electrosurgical generator is bridged to perform a circuit contraction in physical space. Embodiments of the present invention also preferably provide improved system level reliability as there is a significant reduction in the system's dependency upon software for maximum output power governance and emergency shut-down. In some embodiments, the present invention can be used in real-time electrophoresis or drug-infusion (patch) technology (battery powered drug patches that accelerate drug infusion).

With the present invention, a significant reduction in the size of the ESU enclosure is achieved through the reduction of output power governance controls to "state-machine" or simplified software control, both of which reduce the necessary RAM, watch-dog, and Front-Side-Bus speed, requirements of the ESU. All of these reductions in component capacities translate to less circuit board-space being required as parts of equivalent capacity are smaller and require less power to drive at the circuit-board level.

When using RF generators like the Force 2 (ValleyLab), there are four things that stand out and may affect performance from one model of generator to another brand or model (especially newer models), these include:

1. There is no absolute definition of COAG or CUT functions. The waveform (time on/off) and waveshape (being a sinusoid or something else) will vary from model to model.

2. Most generator models have a few types of COAG and these will affect performance and will be available for the user to select. In cases where specific models may have very high COAG output voltages (6,000V-9,000V), reliability/durability questions of device electrical integrity are often raised.

3. The power curve (the power output relative to the electrical impedance seen at the device) of the particular model will have a direct impact on performance. Many older generators have a triangular shaped power curve, such that the power value on the display is only true at a certain impedance. Operating at an impedance larger or smaller than the "ideal" impedance will result in less output power than displayed on the ESU.

4. Newer generators have software controlled power output such that the power curve changes from a triangular shape with a single peak to a trapezoidal shape plateau which is mostly the same output as impedance raises or lowers. These dynamic responses force clinicians to adjust their technique in a concomitant way depending on which device/system pair they are confronted with at the time of any given surgery. Therefore, the power settings are regularly altered, which will again affect performance and may require a lower set power to achieve desired clinical effects when equipment platforms are varied. This is additionally confounded by the change in impedance, capacitance, and temperature at the treatment site by the contact of the active (working) electrode to the tissue that is necessary with prior art devices.

Embodiments of the present invention directly addresses the first three performance variables through reduction of the intrinsic impedance of the overall procedure; by eliminating tissue contact with the active electrode. In the fourth instance the same architectural approach mates well with fast-acting software control to provide yet smoother responses to the ESU that yield stable and predictable electrode operations to the user.

Embodiments of the present invention address three specific categories of features for the design of a plenum chamber in accordance with the present invention:

1. Mechanical. Mechanical features of the plenum housing which provide additional useful surgical features, i.e. sharp, rasp, cutter, potato-peeler like blade, mellon-bailer like scoop, tactile feedback, and general protection of the tissue from the active/working electrode.

2. Fluid Flow. The plenum controls the fluid flow and hence the treatment site reactions. It also allows for the fluid flow to buffer and/or protect the tissue in a cooling manner to avoid the application of excessive heat to the treatment site. The fluid or media can be configured more specifically, like fluids, gels, semi solids and the like that are either conductive or electrolyzable.

3. Electrical. Since the present invention provides the ability for the active/working electrode to operate without touching the tissue, impedance changes far less than in other prior art devices because the tissue, which is the prime driver of impedance change during treatment, is not involved. Impedance fluctuations are buffered so as to better control energy deposition at the treatment site. The present invention also, allows different configurations of the power source, and makes the stability of power deposition at the treatment site safer. Sensing devices are also able to be more effectively used since impedance is no longer necessarily the prime measurement that is used for feedback control. This permits numerous sensors to optionally be used, including but not limited to temperature sensors and pH sensors as more fully described in U.S. patent application Ser. No. 11/006,079.

The general form of the function for impedance of the arthroscopic electrosurgical circuit in-vivo can be approximated by the following generalized function:

$$Z_{TOT}=f[(z_{tissue}+z_{media}+z_{probe}),x,t]$$

If the objective is to understand time-variation of this function it follows that:

$$\frac{\partial Z_{TOT}}{\partial t} = \frac{\partial z_{tissue}}{\partial t} + \frac{\partial z_{media}}{\partial t} + \frac{\partial z_{probe}}{\partial t} + \frac{\partial x}{\partial t} + 0$$

However, in traditional contact electrosurgery, the limits of distance of probe to target tissue site are known to approach zero (i.e. the electrode must contact the tissue):

$$\lim_{x \to 0} \frac{\partial Z_{TOT}}{\partial t} = \frac{\partial z_{tissue}}{\partial t} + \frac{\partial z_{media}}{\partial t} + \frac{\partial z_{probe}}{\partial t} + 0;$$

Additionally, it is important to note that the internal probe impedance with respect to time is effectively a constant:

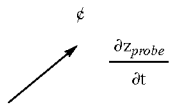

This is because the conductors within the probe consist of stable elements of copper wire conductors whose metallic conductance values (material resistivities) vary little, and therefore do not significantly contribute to the time based variation of impedance.

What remains as the dominant elements of impedance time-based variation is:

$$\lim_{x \to 0} \frac{\partial z_{TOT}}{\partial t} = \frac{\partial z_{tissue}}{\partial t} + \frac{\partial z_{media}}{\partial t} + ¢ \quad \text{(Eq.-1)}$$

Of these elements, the known values for media conductivity (NaCl, 0.09% by weight) are relatively constant even given a relatively small amount of thermal variation in bulk fluid properties (Resistivity typically in the range of 80-110 Ω-cm). This can be restated as: 95Ω-cm±15Ω-cm; illustrating that the relative magnitude of impedance shift (variance) within the media alone represents approximately a 16% variation.

Next, reviewing known parameters of tissue induced impedance in the electrosurgical circuit when in direct contact with probe active electrodes; many electrosurgical manuals indicate that load impedances typically exceed 500Ω into a variety of tissue types. Even under the assumption of equivalent variation (16% of nominal, 500Ω) the total impedance change is equal to 79Ω. This represents a five-fold (5×) increase in overall impedance from that of the interfacing media alone. If we use this nominal approach we can rewrite Eq.-1, above as:

$$\lim_{x \to 0} \frac{\partial z_{TOT}}{\partial t} = 5\left[\frac{\partial z_{media}}{\partial}\right] + \frac{\partial z_{media}}{\partial} + ¢ \quad \text{(Eq.-2)}$$

What this reveals is that during application of RF energy to tissue in domains below plasma, tissue impedance is the dominant factor by at least half an order of magnitude. It is worthy of note, that typical impedance variations have been noted in the laboratory that exceed 30% in tissue contacting electrosurgery which amplifies the stark magnitude difference in Eq.-2 to an even larger extent.

It should now be straightforward to understand that RF electrosurgery, when controlled below plasma levels, provides a more stable impedance environment and enables a more predictable output response of probe technology in relation to applied power. When the benefits of protected electrodes are introduced in below plasma controlled RF electrosurgery Eq.-2 is now dominated only by media impedance variations and is rewritten as follows:

$$\lim_{x \to 0} \frac{\partial Z_{TOT}}{\partial t} = \frac{\partial z_{media}}{\partial} + ¢$$

But this was already identified as being 95Ω-cm ±15Ω-cm, previously. Thus, RF signal/power generator feedback fluctuations for protected electrodes no longer have to deal with rapid and significant swings in Voltage Standing Wave Ratios (VSWRs) and the need for rapid response software control of current flow and voltage output is minimized. FIGS. 1 and 2, below illustrate the differences practically between the Prior-Art and the new State-of-the-Art introduced by NSI.

Embodiments of the present invention provide a protected electrode geometry combined with the reductions in dynamic impedance change that is inherently part of a protected electrode architecture. These embodiments thus provide a more stable platform of low-energy RF electrosurgery below plasma domains. As such, clinicians can benefit from the many and varied applications of RF energy on various tissue types that provide for more complete healing response and lower energy deposition to target tissue sites. These provide the benefit of less harm to healthy tissue and a more complete participation of surrounding tissue, which unharmed by virtue of this architecture, in the overall healing response.

Embodiments of the present invention provide a reduction or elimination of the mismatched impedance of a load in an electrosurgical circuit created by variations that are naturally occurring when tissue contacting electrodes are utilized. Traditional electrosurgery has involved the direct contact of active electrode elements with human tissue where the end result has been to cut, dissect, or ablate the tissue structure. Since the characteristic impedance of such tissue structures is primarily defined by their relative water/electrolyte content (NaCl) as the typical procedure progresses with an electrode in direct contact with tissue, there is a desiccating function that naturally reduces this electrolyte content and thus raises the characteristic impedance during sustained application of RF energy to a target tissue site. This process also induces metabolic effects that the host tissue needs to accommodate.

Typically electrical feedback circuitry built into electrosurgical units (ESUS) are designed to detect high-impedance reflections causing Voltage Standing Wave Ratio's (VSWR) within the primary RF output circuit, defined as:

$$VSWR = \frac{(1 + \Gamma)}{1 - \Gamma},$$

where:

$$\Gamma = \frac{(Z_L - Z_o)}{(Z_L + Z_o)},$$

Note that the source impedance $Z_o$, is essentially that defined by the ESU, connector, cable and the Probe. The Load impedance $Z_L$, is the impedance of the interfacing media, tissue, and return electrode. What becomes evident to those skilled in the art, is the time-varying nature of the impedance and its functionally dependant variables. The raw interfacing media, most commonly NaCl (0.5%-0.9% by weight) has a nominal impedance of 55Ω-100Ω depending on a host of variables that include:

a. Tissue type being contacted (water/electrolyte content)
b. Temperature of the interfacing media
c. Distance of the active electrode to tissue structures
d. Bulk velocity of the fluid field immediately about the active electrode
e. Exposed surface area of the active electrode
f. Distance between the active and return electrodes
g. Random field effects of physio-chemical actions including electrolysis Embodiments of the present invention provide protected electrode probe configurations thus eliminating the variations caused by (a) and drastically limit those caused by (b) above. As contact with tissue is by design prevented, the total impedance variations with time are drastically reduced that could result from tissue desiccation. Current pathways are provided for in the electrode design that can traverse adjacent to tissue from the active electrode to the return electrode through the interfacing media only without affectation by the tissue or its relative conductivity as determined by its state of hydration. This technique as disclosed herein allows for a more specific involvement of the interfacing fluid/media by which the energy of the electrosurgical generator is transferred or deposited at the treatment site. The work of this energy is on the interfacing media primarily, and avoids the higher current densities within tissue of the prior art. These interfacing media interaction are those that would occur within a conductive or electrolyzable media.

When one considers the remaining variables it is clear that (b) and (d) are strongly related as the bulk velocity increases, the temperature will approach the constant of the bulk bag temperature of the saline fluid being infused. Note also that (e) and (f) are fixed quantities based on the specific design of the probe under evaluation. Also note that the protected electrode design limits the minimum distance that the active electrode can be brought toward tissue. The net result is that of the variables at play, in a protected electrode probe design, only (g) remains as a major player in control variables.

For energy levels in the COAG domain (0-180 Watts output power), (g) is nearly linear and increases with output power. This stabilization of large variations in impedance through elimination and reduction of component impedance functions within the electrosurgical environment result in lower VSWR's in the transmission lines of the ESU and Probe. When such conditions are minimized an output circuit is said to be "matched" to its impedance load. While these conditions will not be exact due to the technique dependent factors at play intra-operatively, they are significantly reduced, creating a safer device.

In one embodiment, a preferable distance is from about 0.5 mm to about 5 mm. More preferably, distances of active electrode protection range from about 0.5 mm to about 2 mm.

Non-ablation radiofrequency surgical devices according to an embodiment of the present invention create a repetitive molecular energy conversion loop for surgical work as determined by reconciling the molecular species present; and, non-ionizing electromagnetic forces are deployed at strength levels that can produce thermal and non-thermal biologic tissue effects as determined by the absence of ionizing species detection by typical measuring means. Non-ablation radiofrequency surgical devices are deployed in an immersion setting utilizing a protective housing that prevents electrode-to-tissue contact facilitating electrodes to be fully wetted by the interfacing media. A differential between current density dispersion and electromagnetic field strength is exploited to allow normal tissue healing responses to the near-field effects of tissue modification and preconditioning while permitting far-field effects, which are useful for inducing therapeutic biologic responses, to manifest in treated tissues that have been protected from electrical current generated collateral damage. Embodiments of the present invention provide, based upon procedure-specific needs, the ability to move, manipulate, and segregate near-field effects both tangentially and perpendicularly to the tissue surface; to deliver far-field electromagnetic effects to tissue unencumbered by current deposition; and to serve as a mechanical adjunct to and a selective throttling vent/plenum for energy delivery.

In one embodiment of the present invention, non-ablation radiofrequency energy is used to preferentially increase the density of live chondrons in the Superficial Zone independent of geographic chondrocyte profile and without causing cellular necrosis in tactile soft articular cartilage displaying early lacunar emptying adjacent to fibrillated lesions. In one embodiment, the effects of Non-Ablation radiofrequency energy as characterized by confocal live/dead fluorescence laser microscopy are limited to the Superficial Zone matrix with no evidence of decreased cellular viability or of alterations in geographic chondrocyte profile, chondron image character, or the Transitional Zone. These effects partly reflect a relative preferential extracellular matrix (ECM) modification through a volume contraction; and, provide confirmation of a defined safety margin qualified to the targeting of surface fibrillation lesions with non-ablation radiofrequency techniques. An observed uniform chondron-to-matrix density pattern, illustrate that biologic constraints exist to maintain tissue integrity against the development of focal matrix-failure lesions, resetting functional chondron density patterns in early lesions can create a more chondro-supportive environment for articular chondrocytes as they inherently pursue matrix maintenance and respond to focal disease.

For the surgeon, the earliest visual and tactile cues of articular cartilage degeneration reside in the Superficial Zone, causing this anatomic region to be an appropriate focus for early intervention strategies and placing it into a crucial role for articular cartilage tissue preservation. Because of its distinctive structure and composition, the Superficial Zone is uniquely suited as a therapeutic surgical target from both a diagnostic and a cell-matrix perspective. The Superficial Zone has several layers of varying degree disc-shaped flattened chondrocytes within a matrix of densely packed bundles of thin collagen and elastin fibers oriented parallel-oblique to the articular surface with relatively low proteoglycan content. These layers can serve as physical delamination or cleavage planes between damaged and undamaged areas that can be exploited to stabilize lesions once matrix failure begins to manifest in the most superficial layers. Left untreated and as lesions progress to exhibit further matrix disruption, the resident chondrocytes lose the ability to maintain tissue integrity; conversely, stabilized lesions that preserve Superficial Zone characteristics and viable chondrocytes can retain the healing potential of this zone's cellular phenotype. Preserving viable chondrocytes after lesion stabilization remains important for a matrix modification procedure for early intervention.

The Superficial Zone chondrocyte population retains unique cellular properties depicting a healing phenotype potential to maintain in an early intervention approach to articular cartilage disease. The chondrocyte geographic distribution within Superficial Zone chondrons occurs in distinct patterns with horizontal chondron alignment, consistent with this zone's matrix structure of cleavage planes, rendering it amenable to targeted lesion stabilization from a cellular perspective. When compared to other zonal phenotypes, these chondrocytes demonstrate differences in metabolism, in chondron morphology, in geographic distribution throughout the matrix based upon anatomic location, and in gene expression producing zone-specific molecules like clusterin, proteoglycan 4, and lubricin. The Superficial Zone has been implicated as a driver of chondrocyte migration in response to focal partial-thickness lesions, zonal reorganization, appositional growth, chondroproliferation, chondrocyte colony formation, and a side population source of mesenchymal progenitor cells that express stem cell markers, contractile actin isoforms, progenitor cell signaling mediators, and monolayer expansion behavior while maintaining a chondrogenic phenotype. Treatments that eliminate the Superficial Zone chondrocyte population, like mechanical shavers and thermal or plasma ablation devices, can leave residual Transitional Zone chondrocytes and their accompanying matrix exposed to physiologic demands for which they are not designed to accommodate. Further, a damaged and exposed Transitional Zone does not retain the healing phenotype potential evident within the Superficial Zone chondrocyte population and unnecessarily places an iatrogenic burden upon tissue contiguous to the lesion.

The matrix modification induced by non-ablation radiofrequency applications appears to be a relative ECM rather than a predominant PCM phenomenon histologically. The PCM collagen structure, like its mechanical properties, is uniform with tissue depth in articular cartilage, while the ECM displays zonal and regional inhomogeneities. The PCM in articular cartilage is generally defined by the exclusive presence of type VI collagen defining its boundary with the ECM. Type VI collagen exhibits unique properties which play important roles in mediating cell-matrix and intermolecular interactions. In articular cartilage, type VI collagen serves as an extracellular adhesion molecule that forms a network anchoring the chondrocyte cell membrane to the PCM through its interaction with other extracellular matrix molecules like hyaluronan, biglycan, perlecan, heparin, decorin, and fibronectin. Type VI collagen is responsible for the structural integrity and mechanical properties, like stiffness, of the PCM; and, it can self-assemble into disulfide-bonded dimers and tetramers leading to a distinctive thin-beaded filamentous network around cells. Type VI collagen consists of three different $f_i$-chains and contains a Kunitz-type proteinase inhibitor sequence in the $f_i 3$ chain rendering it resistant to proteolysis. In general, the triple helical conformation of collagen is lost when its temperature exceeds 370 C; but, interestingly, there is evidence that Type VI collagen is partially resistant to heating up to 700 C, is only denatured by heating to 900 C in the presence of reducing agents, and is resistant to depolymerization. These structural nuances help to explain why the PCM appears in this study to be less vulnerable to physiochemical matrix modification than the ECM which is composed primarily of type II collagen and aggrecan. Chondron viability may be protected during a matrix modification that appears to lead chondrons into an increased density pattern by Superficial Zone ECM volume contraction.

Although osteoarthritic changes in the PCM and ECM mechanotransductive properties have been shown to alter the mechanical environment of the chondrocyte, it remains unclear whether the PCM and ECM properties change in a disparate fashion during disease progression; and, how these changes might correlate to the relative matrix failure of early articular cartilage disease. Characterizing these changes will assist in developing matrix modifications that are sensitive to the changes in cell-to-matrix relationships that may alter the stress-strain and fluid-flow environment of the chondrocyte. Because the water volume fraction in articular cartilage is critically dependent upon the function of the Superficial Zone in modulating drag forces, Superficial Zone chondron density continues to be a relevant parameter of functional cartilage as degenerative changes are assessed. The biologic role of structural matrix alterations has been the subject of recent modeling studies. Additional attention toward the lamina splendens is also important, particularly due to the unique role its interwoven collagen network plays in modulating proteoglycan content and subadjacent collagen network orientation that is accessible during Superficial Zone lesion stabilization. The observation that chondrocytes adhere to areas of lamina splendens disruption and the combined biomechanical effects of wear-line and split-line orientation warrant further investigation for early intervention strategies.

Figure 21A:
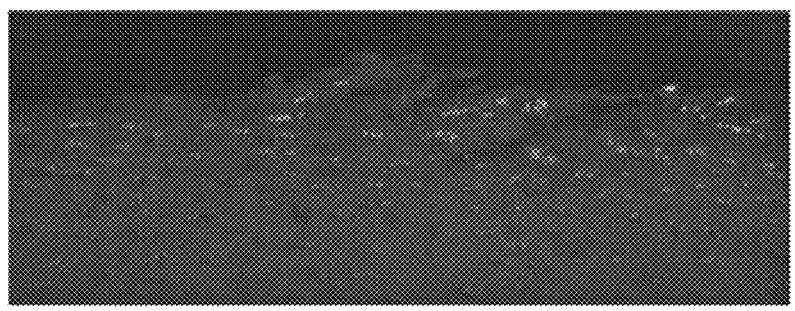
FIGS. 21A and B are images which respectively illustrate targeted removal of surface fibrillation prior to and after treatment.
Figure 21B:
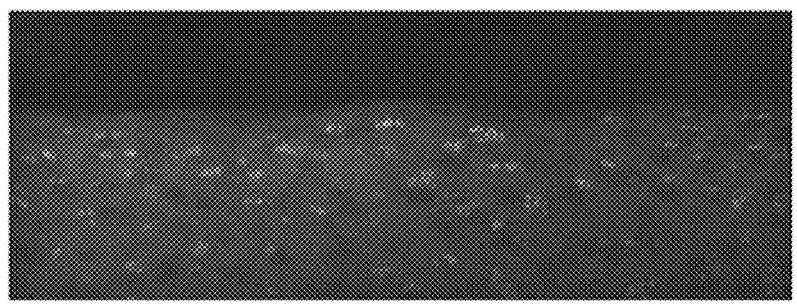
Figure 28:
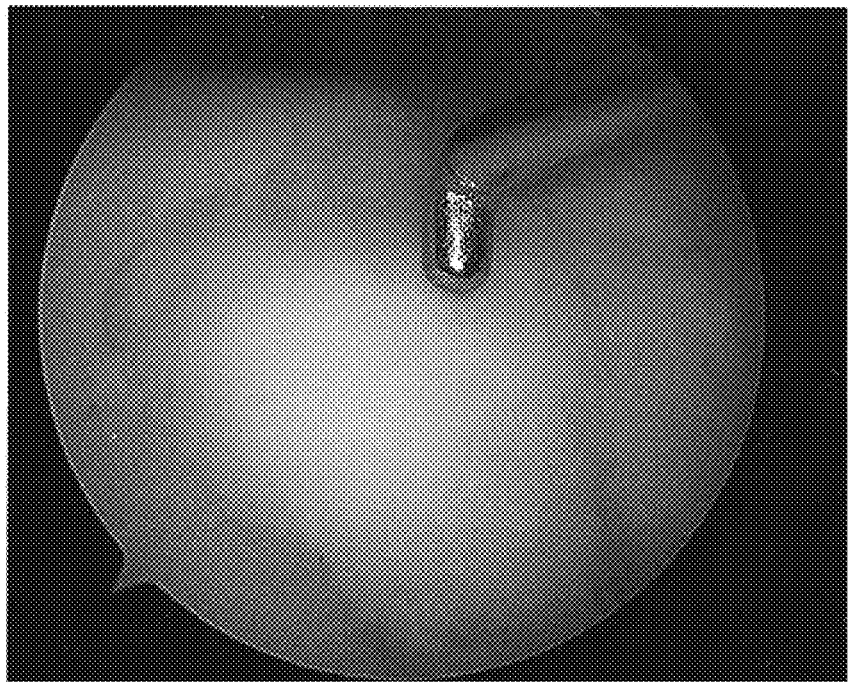
FIG. 28 illustrates an intra-operative photograph during second-look arthoscopy.

Chondrocyte depletion, whether by apoptosis, necrosis, or other mechanisms, may be a predisposing condition to surface fibrillation as noted in the adjacent regions of the tissue harvested for this study. As illustrated in FIG. 21, surface fibrillation often demonstrates intact chondrons within the fibrillation itself, with extruded chondrocytes uncommonly noted in areas within and around the surface fibrillation. This data provides some evidence that overt ECM failure rather than primary PCM failure is the early condition presented to the surgeon for treatment consideration. Early intervention remains attractive particularly since full-thickness lesions have received significant attention and may be the next opportunity for which tissue preserving intervention might be considered. Interestingly, a confluence of cell-to-matrix interaction research has been observed through the treatment of articular cartilage with electromagnetic energy. Chondrocyte proliferation, gene expression modification, temporal changes in matrix production, and lacuna formation in response to single exposure electromagnetic fields has been shown, which is consistent with observations of a cartilage response to voltage potential delivery at the disease locale of full-thickness defects. FIG. 28 illustrates that these clinical responses occur more reliably for margin-intact lesions, implicating the resident Superficial Zone in the healing response observed for full-thickness lesions. These responses might serve as a target substrate for non-destructive electromagnetic energy induced host-to-implant lateral integration as an adjunct to implant-to-host approaches pursued for full-thickness defects. Not only does the healing potential phenotype of the Superficial Zone provide treatment substrate options for Superficial Zone and full-thickness lesions, it can also provide additional treatment substrate options for Transitional Zone lesions surrounded by an intact Superficial Zone.

Although the description above contains many specific examples, these should not be construed as limiting the scope of the invention but merely providing illustrations of some of the presently preferred embodiments of this invention. Thus, the scope of the invention should be determined by the appended claims and their legal equivalents, rather than narrowed by the specific illustrative examples given.

Industrial Applicability:

The invention is further illustrated by the following non-limiting examples.

EXAMPLE 1

The effects produced by surgical devices that deploy an electrical circuit between electrodes are dependent on the nature of electrical work performed upon the conductive media in and around biologic tissues. Because this conductive media is water-based, examples of the present invention characterize the effects that non-ablation radiofrequency energy exerts upon saline interfacing media typically encountered during surgical applications. Non-ablation radiofrequency surgical devices were deployed in a bulk 0.9% sodium chloride solution at 300 mOsm/L at 20° C. During energy delivery, temperature and pH changes; gaseous species production, gas condensation behavior, and gas generation dynamics; and ionized charged particle generation were measured in the region of a constrained primary reaction zone surrounding an active electrode. Saline temperature change demonstrated three functional domains commensurate with a decrease in pH at steady-state at the constrained primary reaction zone without changes to the bulk fluid. Gas chromatography, thermal conductivity detector, and flame ionization detection evaluations measured a uniform 2:1 ratio of hydrogen and oxygen comingled non-condensable gas production indicative of split water without heat transfer or gas generation dynamics of water vapor. The presence of ionized charged particles was not detected. These results allowed formulation of a stoichiometric model depicting a repetitive molecular energy conversion loop from water under non-ionizing electromagnetic forces. Non-ablation radiofrequency applications utilize the energy from the molecular bonds of interfacing media water to perform surgical work without delivering ionizing electromagnetic radiation.

FIG. 11 illustrates a representative non-ablation radiofrequency surgical device exhibiting a protective housing that prevents active electrode-to-tissue contact, ensuring direct energy delivery to the saline interfacing media at the electrode surface. The electrode comprises stainless steel and a small amount of titanium (for example about 0.5%) used to stabilize its structure at higher temperatures, to prevent carbide precipitation from the grain boundaries, and to protect the metal from corrosion. The protective housing comprises an electrical and thermal insulating ceramic which prevents electrode-to-tissue contact and creates a constrained primary reaction zone around the surface of the active electrode. The devices are configured in a bipolar fashion by connecting to an electrosurgical generator delivering radiofrequency energy at varying power outputs (for example, a small fraction of a watt to about 350 W), voltage potentials of from about 0.1 kV to about 4.5 kV, and frequencies of from about 100 kHz to about 1 MHz. A general distinguishing characteristic of non-ablation, when compared to ablation, radiofrequency energy is a low current density bias combined with a high voltage potential bias. The area within the ceramic insulator and around the active electrode is the primary reaction zone wherein the saline interfacing media is worked upon by the radiofrequency energy. Electrical current is delivered to the interfacing media at the electrode surface and the precipitant reaction products can be directionalized by the configuration of the ceramic insulator openings to the treatment site. Note that in one embodiment, the active electrode does not protrude from the edge of the ceramic housing.

Figure 12:
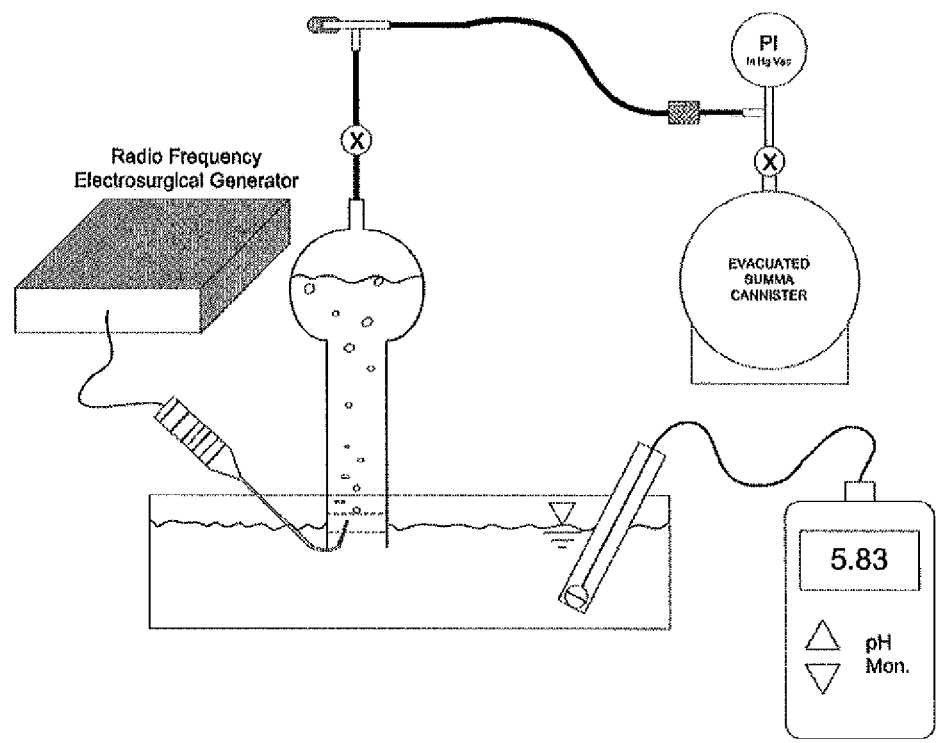
FIG. 12 is a schematic illustration of an experimental laboratory set-up designed to evaluate the near-field effects of non-ablative radiofrequency manipulation of saline interfacing media.
Figure 13:
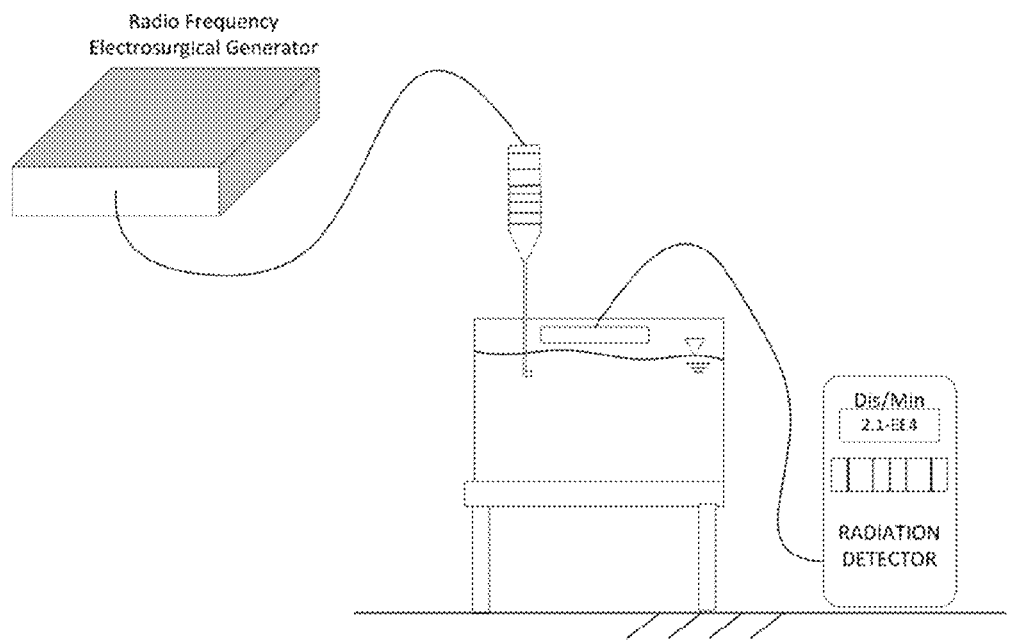
FIG. 13 is a drawing illustrating an experimental laboratory set-up designed to determine whether generation of charged particles occurs with non-ablative radiofrequency manipulation of saline interfacing media—the distances between the electrode and the water surface are exaggerated for purposes of illustration.
Figure 14:
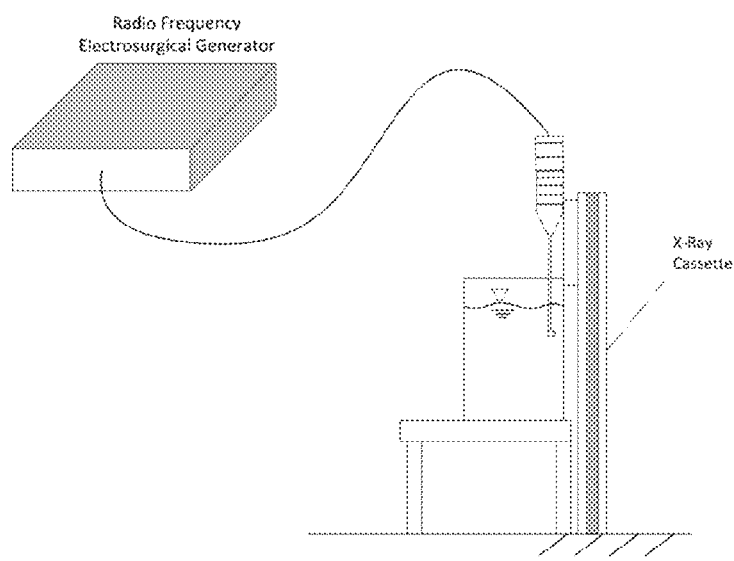
FIG. 14 is a drawing which illustrates a time integrated experimental laboratory set-up designed to determine whether generation of charged particles occurs with non-ablative radiofrequency manipulation of saline interfacing media; the distances between the electrode and the roentgenographic wall are exaggerated for purposes of illustration; the americium-21 control source is not illustrated in the drawing.

The devices were tested in the apparatuses illustrated in FIGS. 12-14 with the device tips fully immersed in bulk 0.9% sodium chloride at 300 mOsm/L at 20° C. typically used during surgical applications. During testing, the devices were driven to steady-state conditions unless otherwise noted.

The apparatus of FIG. 12 was used to evaluate the near-field effects of non-ablation radiofrequency energy that occur at the active electrode surface within the primary reaction zone of the protective tip housing. Temperature and pH changes of the interfacing media were measured in both the primary reaction zone at the protective housing opening and the bulk solution away from the device during probe activation. Produced gas was collected and analyzed by ASTM D-1946 gas chromatography, thermal conductivity detector, and flame ionization detection evaluations (GC/TCD/FID) for constituent species. A separate glass container of collected gas was allowed to stand at ambient conditions to determine condensation behavior as an additional determinant as to whether water vapor was present.

For purposes of illustration, in FIG. 12, the pH detector is illustrated as being disposed away from the probe's primary reaction zone. The temperature probe is not illustrated in FIG. 12. The temperature and pH of both the primary reaction zone and the bulk solution was measured independently. The gas collection process included an inverted glass collection tube fully filled with the same interfacing media as in the reaction reservoir to create a manometer fluid column that could be displaced by collected gas. Generated gas bubbles were allowed to naturally float into the capture section of collecting tube via buoyancy forces to displace approximately 95% of its total volume. Thereafter, the gas was evacuated from the collection tube by partially opening the stop-cock valve to form a restriction and then sequentially opening the needle valve allowing the gas to fill the summa canister. The combined flow restrictions allowed inlet gas rate metering to avoid unwanted water uptake into the summa canister. The summa canister was allowed to maintain an intact partial vacuum with an attached pressure gauge so that the receiving laboratory could verify whether inadvertent uptake of contaminating atmosphere had occurred during transport.

Gas generation dynamics at the electrode surface were characterized by video assessment and digitized using a 1188HD 3-Chip camera to allow comparison to a control of water vapor bubble production typical of ablation-based radiofrequency devices. Bubble time to release state from the electrode, diameter and volume, shape and conformational fluctuation, coalescent tendencies, directional mass transfer fluid delivery properties, and relative terminal velocity were assessed qualitatively.

The apparatus illustrated in FIG. 13 was used to evaluate the far-field effects of non-ablation radiofrequency energy that might occur within the electromagnetic fields generated by the surgical device as a result of the near-field energy conversions. The production of ionizing electromagnetic radiation was monitored using a radiation particle detector in the treatment field sensitive to 200 disintegrations per minute at 1 mm distance from the air-water interface, a distance over which a 0.5 keV particle would be transmitted as the removal of shell electrons emits characteristic energies from a few keV to over 100 keV. This sequential phase interface design allowed particles to be detected if produced in any appreciable quantity above normal background radiation. The device was activated for a continuous 30 minutes.

FIG. 14 illustrates an apparatus that was used to time integrate roentgenographic film exposure by ionizing electromagnetic particle generation. The surgical device was fully immersed and placed with the active electrode within 1 mm of the roentgenographic cassette wall of the reservoir and activated for a continuous 30 minutes allowing any ionized reaction zone species to integrate over time and expose the film. A control emitter source of alpha ($\alpha$) particles and low energy gamma rays of 60 keV, americium-241, was adhesively affixed to the roentgenographic wall with the same spacing of 1 mm to demonstrate time dependant control exposure.

Figure 15:
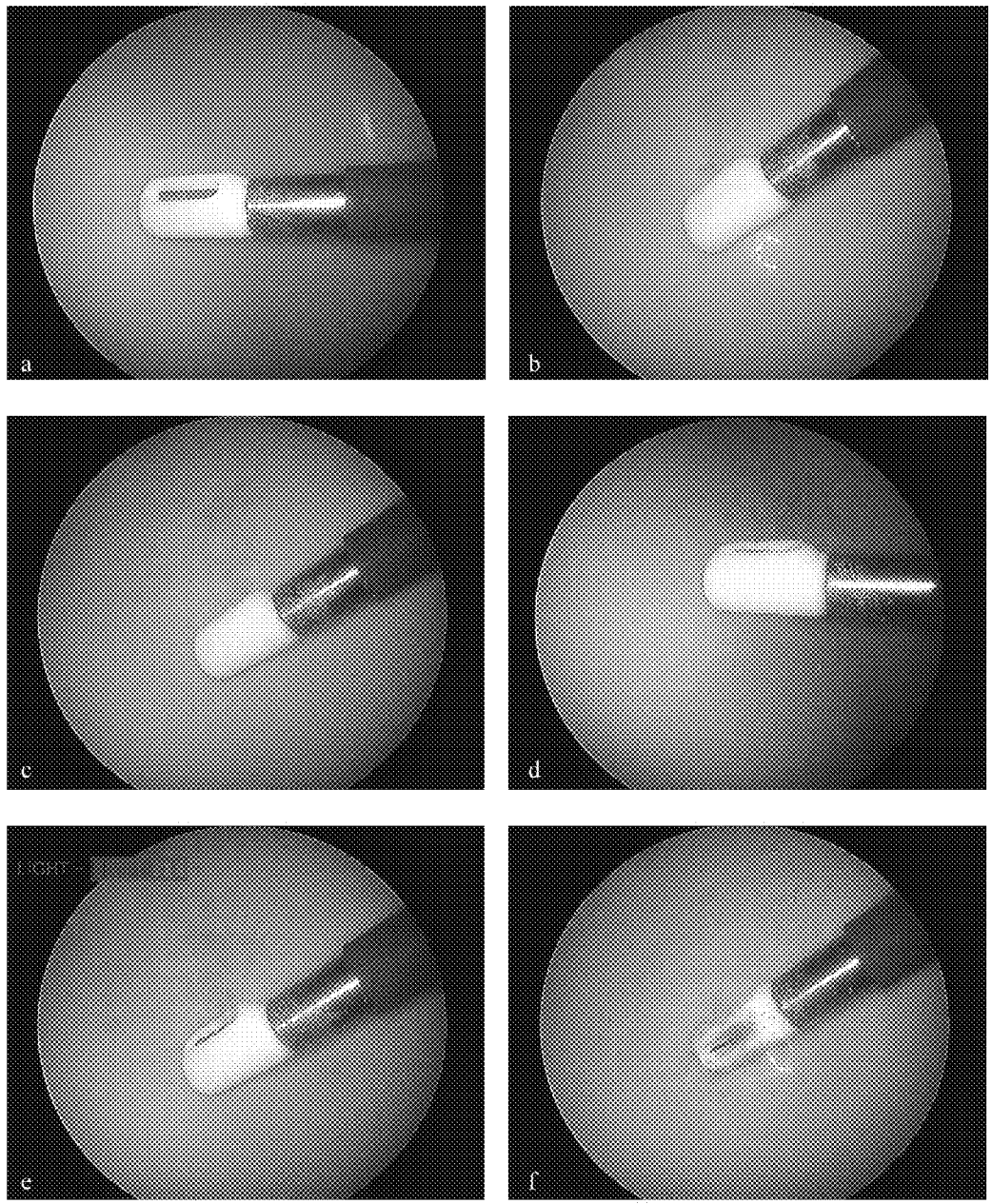
FIGS. 15A-F are images illustrating non-ablation radiofrequency energy manipulation of saline interfacing media, including electrothermal, electrochemical, and gas generation dynamics at power deliveries of 0 Watts; 25 W; 50 W; 75 W; 100 W; and 120 W respectively.

Two non-ablation radiofrequency energy conversion modes were evident based upon visual cues that can be used to define surgical work on water: One during which the device deploys energy levels that do not produce non-soluble gas; the other during which non-soluble gas is produced. As demonstrated in FIG. 15, these modes were part of an observable continuum that was dependent upon power level applied to the interfacing media. In all instances, a steady state was achieved with probe activation by 3 seconds. The threshold for non-soluble gas production detectable by gross visualization was a power delivery of 35 W. Voltage and frequency influences on steady state for a given power delivery level did not significantly alter the threshold for gas production within the ranges tested. As noted in the images of FIG. 15, early non-soluble gas (bubble) production does not begin until a power of about 35 W was achieved, after which the non-soluble gas production level remained consistent without overwhelming the dynamics of the primary reaction zone until 75 W, when the turbulence and mass effect of the increased gas production facilitated the removal of the reactants/products from the primary reaction zone more dramatically.

Figure 16:
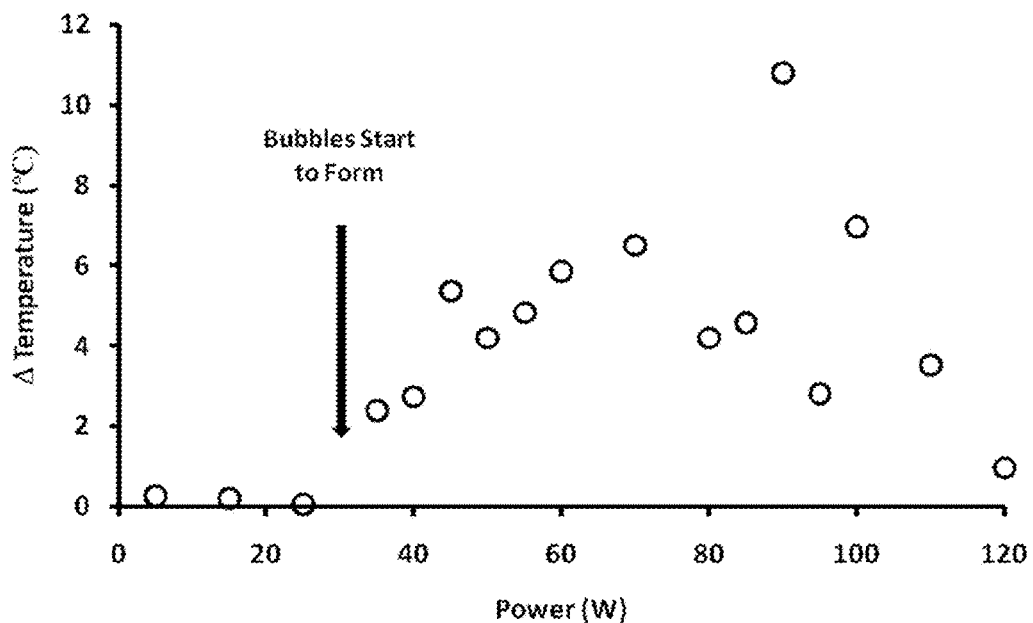
FIG. 16 is a graph illustrating temperature changes versus power delivery at the primary reaction zone when non-ablation radiofrequency energy was delivered to saline interfacing media.

Electrothermal effects of the primary reaction zone are illustrated in FIG. 16. Temperature at steady-state was generated well below the level at which water vapor could be produced. The thermal gradients migrated from the electrode based upon typical thermodynamic behavior but could be altered by the configuration of the protective housing. The bulk saline bath did not change temperature significantly during the testing with probe activation. As illustrated in the graph of FIG. 16, the temperature distribution demonstrated three distinguishable functional domains: the first domain (0-35 W) revealed no temperature change associated with the lack of non-soluble gas formation; the second domain (35-75 W) revealed a linear relationship of temperature increase during low-level non-soluble gas formation; the third domain (75-120 W) revealed a decrease in temperature associated with more pronounced non-soluble gas formation despite the increased power delivery to the primary reaction zone.

Figure 17:
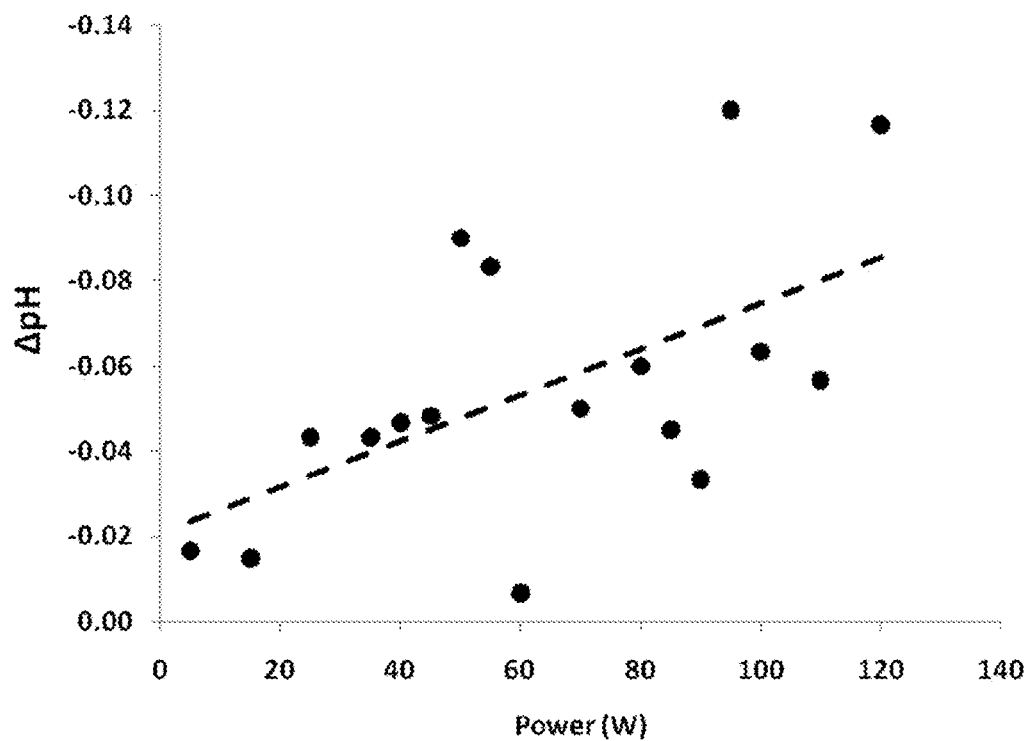
FIG. 17 is a graph illustrating pH changes versus power delivery at the primary reaction zone when non-ablation radiofrequency energy was delivered to saline interfacing media.

Electrochemical effects of the primary reaction zone are illustrated in FIG. 17. These effects were evident visually as a pH fluid wave with the acid-base shift migrating based upon typical solution densities, but could be directionalized based upon configuration of the protective housing (see FIG. 15 noting the varying probe positions). The pH of the primary reaction zone demonstrated a linear relationship between power delivery and unit pH drop until energy delivery was terminated at which time rapid normalization occurred. The bulk saline bath did not change pH significantly during the testing with probe activation. $R^2=0.311$; $p<0.02$. Note that the goodness-of-fit linear regression is better for the segment during which low level non-soluble gas formation occurs (35-75 W) with increasing scatter as the primary reaction zone turbulence increased.

From about 0 to about 35 W of energy delivery (Phase 1), non-soluble gas was not produced, temperature did not increase, but pH decreased. From about 35 W to about 75 W (Phase 2), non-soluble gas was produced at levels that did not overwhelm the dynamics of the primary reaction zone commensurate with a linear temperature increase and linear pH decrease. From about 75 W to about 120 W (Phase 3), non-soluble gas production increased to a level that overwhelmed the primary reaction zone dynamics and was associated with a decrease in temperature despite the increased energy delivery and a more scattered but linearly decreasing pH.

ASTM D-1946 GC/TCD/FID analysis yielded uniform species results in all instances with a 2:1 ratio of hydrogen and oxygen comingled gas without significant atmospheric contamination or evidence of water vapor. The collected gas was not condensable within the separate glass collection container confirming the ASTM D-1946 GC/TCD/FID analysis lacking water vapor.

Figure 18:
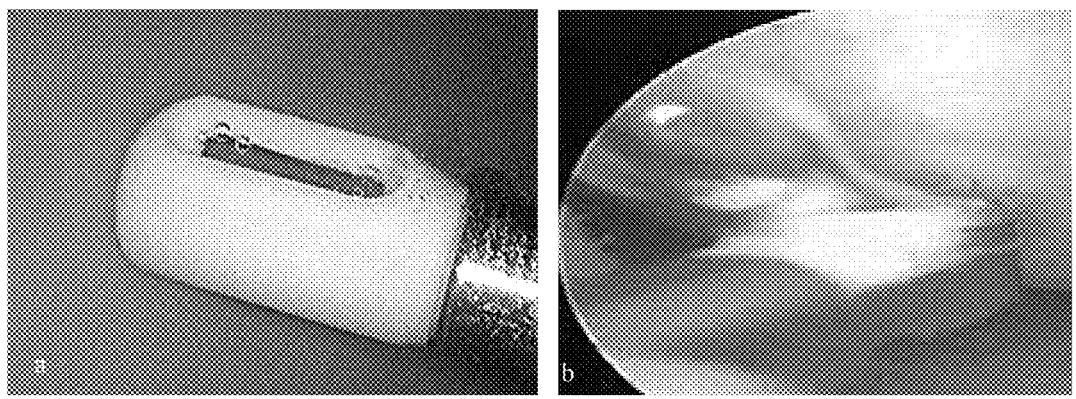
FIGS. 18A and B are images of gas general dynamics of non-ablation (a) versus ablation (b) radiofrequency energy deposition upon saline interfacing media.

Consistent with the constituent make-up of the collected gas, the gas bubble dynamics were different from that of water vapor bubble production used as a control as noted in FIG. 18. When compared to water vapor bubble generation, the comingled oxygen and hydrogen gas bubbles reached release state from the electrode very rapidly, were small in size on the order of a 125× smaller volume, remained spherical without confirmation fluctuations typical of the much larger water vapor bubbles, did not coalesce with other bubbles, demonstrated directional mass transfer fluid delivery properties, and displayed a slower terminal velocity. Gas bubble flow dynamics were easily modulated with the protective housing throttling vent/plenum (see also FIG. 15). The ablation electrode is illustrated at tissue contact during use; whereas the non-ablation electrode is illustrated without tissue present as it cannot touch tissue during use. The larger bubble in (a) has a diameter of about 0.3 mm; the singular bubble in (b) has a diameter of about 3.9 mm. Water vapor bubbles (b) typically were larger, with a surface tension, adhesion dependant stalk connecting it to the electrode prior to release.

During operation, particles were not sensed by the radiation particle detector above standard background, which averaged approximately 2.5 mSv/yr at the testing locale. After 30 minutes of exposure to both non-ablation radiofrequency energy deposition and americium-241 source, only the americium-241 source area was exposed. The area immediately adjacent to the electrode remained unexposed and clear of any image. Non-ablation radiofrequency energy produced only non-ionizing electromagnetic forces.

Figure 19A:
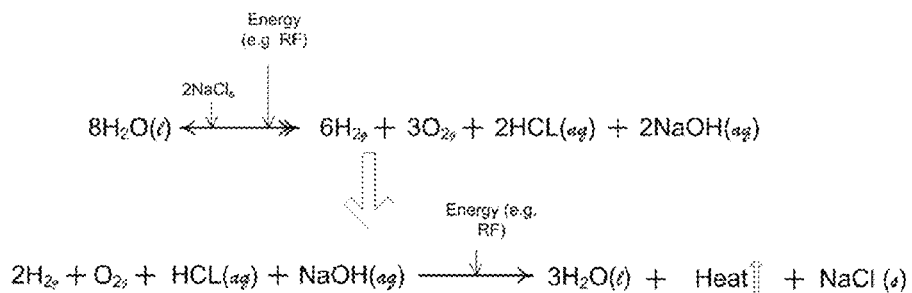
FIGS. 19A-D are stoichiometric equations illustrating reactions according to an embodiment of the present invention.

The defined reactants (0.9% sodium chloride aqueous solution, radiofrequency energy) and resultant products (2:1 ratio of $H_2$ and $O_2$ gas, pH drop, heat) present in this study, along with the generation dynamics and lack of ionizing electromagnetic radiation observed, allow formulation of a uniform stoichiometric thermochemical description of non-ablation radiofrequency deposition upon saline interfacing media. This formulation is illustrated in FIGS. 19A-D. FIG. 19A is stochiometry of the near-field effects of non-ablative radiofrequency manipulation of saline interfacing media. Two half-reactions of the thermochemical cycle that describe the quantitative relationships between the reactants and products for the repetitive molecular energy conversion loop [(aq)=aqueous; (g)=gas; (I)=liquid; (s)=solute].

Figure 19B:
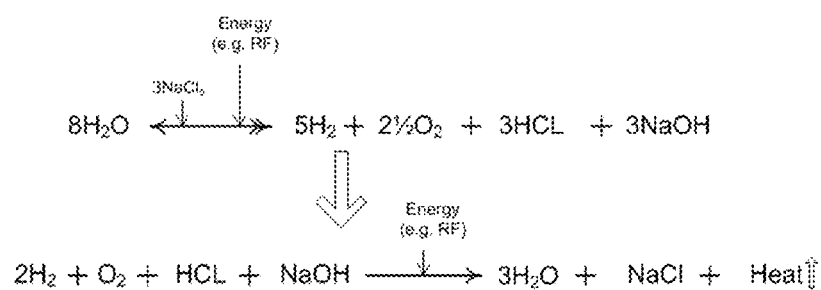

The overall process utilizes alternating current to rapidly split and reconstitute water in a repetitive molecular energy conversion loop. The general, electrothermal, electrochemical, and gas production observations are governed by the relative availability of the reactants and products within the primary reaction zone. The initial splitting of water is slightly endothermic driven by the low current and high activation overpotential of non-ablation radiofrequency energy. In this setting, gas emanation is inefficient as bubble threshold fluencies and bubble lifetime dictate aqueous nano-sized bubble production that are immediately converted back to water. As gas emanation is produced, bubble size remained very small with high release rates; therefore, the electrode-to-water interface surface area was not significantly altered by gas production at any setting thereby limiting significant electrode current density or impedance fluctuations. This phenomenon was further supported by the high voltage potentials delivered which diminish any minimal effect of bubble induced conduction area reduction. As gas emanation occurred and gas was liberated from the primary reaction zone by buoyancy forces, complementary liberation of additional acid-base pairs necessarily occurs, both of which may be modulated by the protective housing throttling vent/plenum. FIG. 19B illustrates that the loss of reactants or products from the primary reaction zone, such as gas emanation modulated by the protective housing throttling vent/plenum, can cause the electrochemical effects to become more visible. These electrochemical effects are termed an acid-base shift.

Figure 19C:
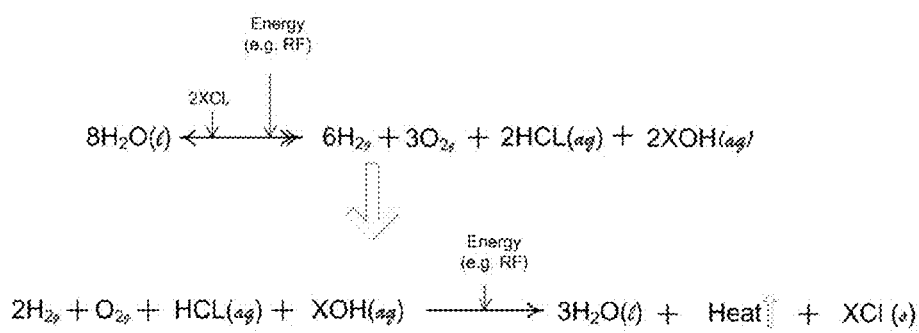

FIG. 19C illustrates a more general case in which the ionic salt is represented by variable X, where X is any appropriate group 1, period 1-7 element of the periodic table. The salt-bridge catalytic efficiency is dependent upon the salt's elemental properties. [(aq)=aqueous; (g)=gas; (I)=liquid; (s)=solute].

Figure 19D:
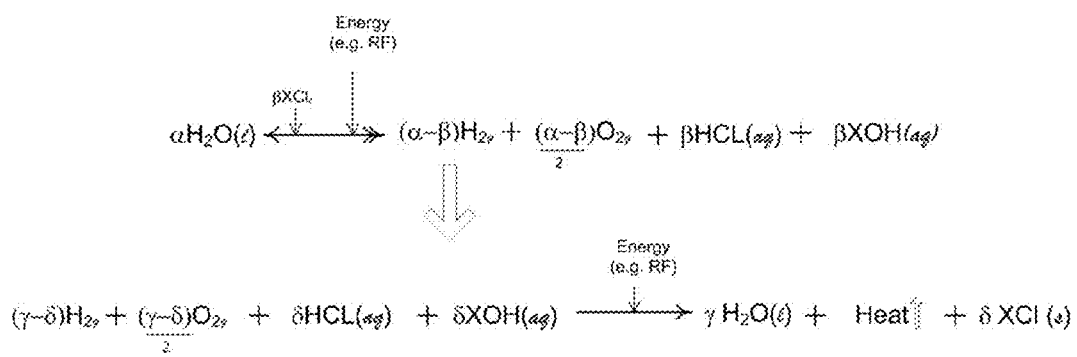

FIG. 19D is a drawing illustrating the repetitive molecular energy conversion loop having variables consisting of $\alpha$, $\beta$, $\gamma$, and $\delta$ wherein, the molar quantities required are any value that appropriately satisfies the oxidation reduction valence requirements for the overall reaction. [(aq)=aqueous; (g)=gas; (I) =liquid; (s)=solute].

Figure 20:
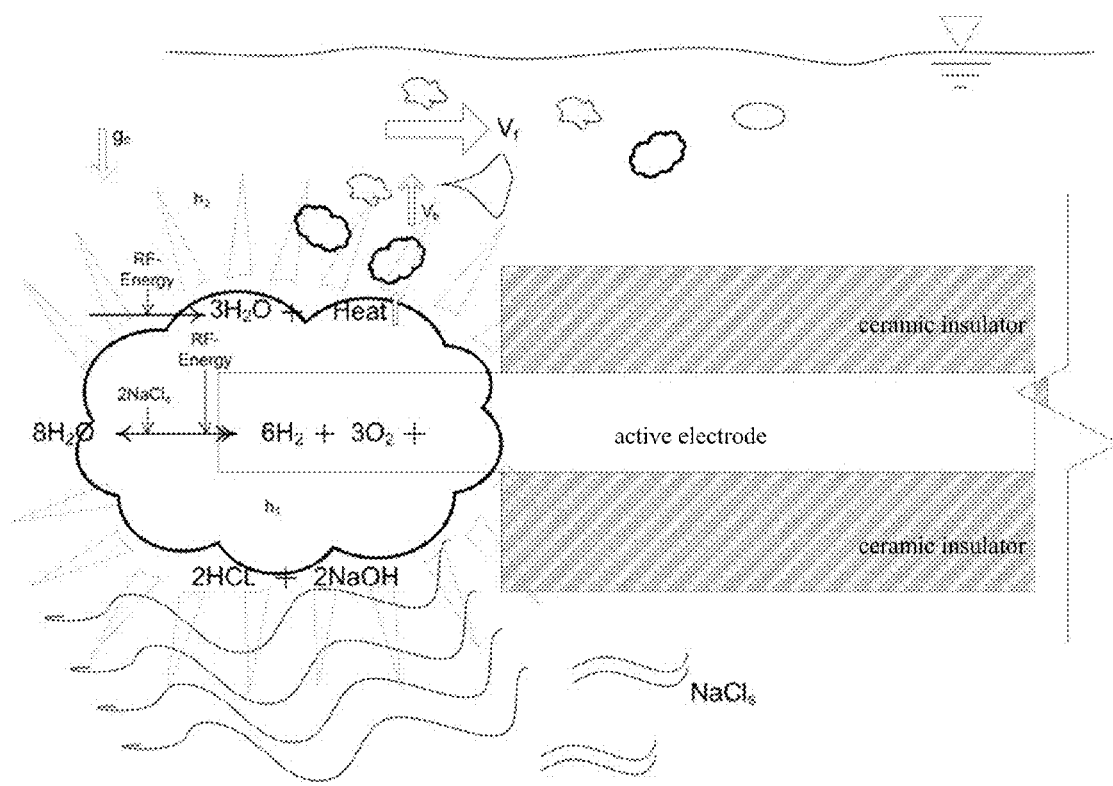
FIG. 20 is a drawing which illustrates a representational model summarizing non-ablation radiofrequency energy manipulation of saline interfacing media with overlaid equations on the depicted physical flow-field of surgical application.

Referring now to FIG. 20, the electrode provides conducted electrical energy to the electrode-water interface through a salt ion solution whereby water splitting causes the accumulation of oxygen and hydrogen gases immediately about the electrode which rapidly reduce to water and heat. As the reaction takes place, buoyancy forces allow non-soluble gas to escape the primary reaction zone; while acid-base pairs of greater density descend away from the electrode with artifacts visible as density streak-lines. As the acid-base pairs move away from the electrode, cooling takes place which results in a normal precipitation. This reactant-product escape, although modulated by the protective housing, is facilitated by normal fluid flow in the surgical environment that, in addition, simultaneously induces considerable reaction zone quenching while preventing reaction zone water-starvation. Therefore, the repetitive molecular energy conversion loop does not result in any volumetric loading of the primary reaction zone. This reaction is not possible to deploy without the protective housing around the active electrode due to the large fluid flow fields present during surgical application.

Phase 1 observations (0-35 W, inefficient water splitting, limited water reconstitution)

At this energy input level, alternating current is very inefficient at splitting water and producing non-soluble gas, an endothermic reaction. Non-soluble gas is not produced indicating the reaction zone has yet to reach gas saturation characteristics to generate non-soluble gas production. Therefore, the reconstitution of water, an exothermic reaction, does not occur to a level that would demonstrate a significant increase in temperature at the unconstrained edge of the protective housing. The noted decrease in pH is indicative of water splitting.

Phase 2 observations (35-75 W, efficient water splitting and reconstitution)

Increasing alternating current delivery becomes more efficient at splitting water as non-soluble gas is produced consistent with gas saturation characteristics of the primary reaction zone. Therefore, more split water is available for reconstitution, producing an increase in temperature as power increases consistent with the increased frequency of water reconstitution, an exothermic reaction. pH continues to drop consistent with the process of splitting water and reactant/product migration from the primary reaction zone.

Phase 3 observations (75-120 W, more efficient water splitting and less efficient water reconstitution)

Further increasing alternating current induces even larger amounts of non-soluble gas production facilitating increased primary reaction zone turbulence and mass transport effect removing reaction reactants/products from the primary reaction zone more rapidly. This non-soluble gas removal and increased acid-base shift decreases the efficiency of water reconstitution which in turn decreases the frequency of exothermic water reconstitution resulting in the noted temperature decrease. pH continues to drop consistent with the process of splitting water and reactant/product migration from the primary reaction zone, although more scattered based upon the altered primary reaction zone dynamics.

FIG. 20 is a Diagrammatic representation of the manipulation of saline interfacing media by non-ablative radiofrequency energy. Note that the protective housing is not shown for the purposes of illustration. Ablation devices have exposed electrodes making any attempt at low energy physiochemical conversions inconsequential due to the large physical fluid flow and convective forces present during surgical application; hence their design necessitates a large amount of energy delivery. Faded triangles represent electrothermal effects; wavy lines represent electrochemical effects. $V_f$ represents the convective force velocity of the fluid flow outside of the protective housing; $V_b$ represents bubble buoyancy force velocity of non-soluble gas production; $g_c$ represents gravitational forces exerted upon the denser acid-base precipitants; $h_1$ represents electrothermal heat within the protective housing; and $h_2$ represents the electrothermal heat that may leave the primary reaction zone.

The results of this experiment demonstrates that non-ablation radiofrequency energy produces distinct near-field and far-field effects as electrical energy is converted to a therapeutically useful form. Near-field effects to perform surgical work are created by a thermochemical cycle originating directly from the molecular bond energy of water. This electrosurgical refinement creates an energy efficient procurement system that is a sister technology to other methods designed to capture released molecular energy from water like fuel cells, photolysis, and photosynthetic machinery. Non-ablation surgical devices utilize alternating current to rapidly split and reconstitute water in a repetitive molecular energy conversion loop as a means to modify or precondition biologic tissues. Active electrode current density dispersion is manipulated by the protective housing to limit current delivery into tissues as current can be detrimental through tissue electrolysis and/or resistive (ohmic or Joule) heating. The near-field effects of current are delivered to the tissue surface rather than relying upon an electrode-to-tissue interface as in ablation-based devices designed to eliminate, coagulate, or dissect tissues. Because the near-field effects of current are geographically constrained within the protective housing, these effects can be manipulated based upon procedure-specific needs with the protective housing serving as a mechanical adjunct to and selective throttling vent/plenum for energy and reactant-product delivery. The devices allow far-field electromagnetic forces to manifest within tissue unencumbered by current deposition and which are of intensities that do not create ionizing forces. A differential between current density dispersion and electromagnetic field strength is exploited to allow a normal healing response of tissues in reaction to the near-field treatment effects of tissue modification and preconditioning, while permitting far-field effects designed to induce therapeutic responses in the treated tissues that have been protected from the collateral damage of electrode-to-tissue interfaces.

EXAMPLE 2

Radiofrequency energy was delivered by two methods for both 5 second and 10 second durations to ex-vivo femoral condyle osteochondral specimens obtained from patients undergoing total joint replacement; Ablation and Non-Ablation. Untreated control and treated specimens were sectioned, prepared with Live/Dead cell viability stain, and assessed by confocal fluorescence laser microscopy. The results of this example showed that the mean total Superficial Zone cell number in control sections was 1480 per $mm^2$. The Ablation method fully corrupted the Superficial Zone by volumetric loss or near complete cellular necrosis with a mean post-treatment depth of necrosis of the remaining residual cartilage at the treatment site of 140 fÊm (range 104 fÊm-199 fÊm) at 5 seconds and 226 fÊm at 10 seconds (range 140 fÊm-334 fÊm) through the Transitional Zone tissue. The Non-Ablation method retained the Superficial Zone with a mean total number of cells of 1468 per $mm^2$ (no statistical difference from control) with a 12% increase in live chondron density of over control ($p<0.02$). Chondrocyte viability, intrachondron chondrocyte geographic pattern, chondron image character, and the Transitional Zone was not altered in the non-ablation treatment group; the increased live chondron density partially originated from preferential extracellular matrix volume contraction of the Superficial Zone. These findings illustrate that non-ablative radiofrequency energy can preferentially increase articular cartilage Superficial Zone live chondron density. The Superficial Zone extracellular matrix, because of its distinctive composition, is uniquely suited to manipulative structural reorganization. Resetting functional chondron density patterns may have the potential to create a more chondro-supportive environment for articular cartilage as it inherently responds to focal disease.

Osteochondral femoral condyle specimens were harvested from patients undergoing total knee replacement under an approved Institutional Review Board protocol. Specimens were included that demonstrated an area of uniform tactile soft chondromalacia adjacent to areas of surface fibrillation (partial thickness damage) of sufficient size from which test samples could be obtained that demonstrated geographically similar characteristics. After harvest, specimens were divided and each part was randomly sequestered into a treatment group and immediately transferred to an ex vivo arthroscopic treatment setting. Three treatment groups were established with a part from each specimen: Control (which received no treatment), Ablation (thermal and plasma ablation), and Non-Ablation.

Each treatment group was assigned its own station with an ex vivo arthroscopy set-up. Standard arthroscopic fluid was used at room temperature with a fluid-flow rate of 30 cc/min } 5 cc/min which created consistent fluid dynamics in the set-up typical of in vivo arthroscopy. The flow was measured and recorded at each station throughout the study and was maintained constant for all testing. The radiofrequency systems were used at the generator settings recommended by their manufacturer's design: thermal and plasma Ablation included GliderR (Smith and Nephew, Inc.; Andover, Mass.) and ParagonR (Arthrocare, Inc.; Austin, Tex.); Non-Ablation included CeruleauR (NuOrtho Surgical, Inc.; Fall River, Mass.).

Treatment of the tactile soft cartilage surfaces was performed by one practicing surgeon accustomed to radiofrequency debridement chondroplasty. The goal of the treatment was to utilize the same technique typically deployed to remove fibrillated cartilage and smooth the articular surface as determined by visual cues. Energy delivery treatment time was divided into 5 and 10 second groups with a technique of moving the probe tip back and forth at the treatment site with a consistent application pressure and speed as judged by the surgeon to mimic in vivo treatment conditions. With the ablation devices, the surgeon used the active electrode as a mechanical implement for gentle electrode contact, consistent with their design, by moving the electrode across the articular surface during the allotted energy deposition time. With the Non-Ablation system, the surgeon used the protective housing edge to mechanically brush the surface of the tissue concurrent with energy delivery for the allotted treatment time. Immediately after each treatment, three 0.5 mm coronal sections of each sample were obtained referencing the center of the treatment site. The sections were prepared for staining by washing in a buffered saline solution. Live/DeadR Reduced Biohazard Cell Viability Kit #1 green and red fluorescence, SKU #L-7013, (Invitrogen., Carlsbad, Calif.) was used per manufacturer's specification to stain specimens. Specimens were gluteraldehyde fixed, transferred to standard flat glass slides, and flooded with VECTRASHIELDR brand fluorescence protection oil prior to the placement of #1.5 borosilicate glass cover slips over each specimen section.

Confocal fluorescence laser microscopy analysis was performed by personnel blinded to the identity of the treatment groups for each specimen part. Confocal imaging was performed with an Olympus IX-81 inverted microscope coupled to an Olympus FV300 confocal laser scanning unit (Center Valley, Pa, USA) using 488 nm laser excitation. Live cells were captured under green fluorescent channel (505-525 nm) and dead cells were captured under red fluorescent channel (577-634 nm), generating a Live image, a Dead image, and an Integrated Live/Dead image.

The extent of collateral damage induced by each treatment was determined based upon both the amount of initially non-damaged cartilage tissue removed from the treatment site when compared to control specimens and the condition of the residual tissue remaining at the treatment site. Depth of necrosis of the residual tissue post-treatment for both the 5 and 10 second groups was determined by measuring the distance from the center of the residual tissue surface after treatment to the lowest depth of dead cells observed. Total number of cells, number of dead cells, and number of live cells per $mm^2$ were counted for the treatment site of each group. Chondrocyte geographic profile (i.e. single, pairs, strings, or clusters) and chondron image character (i.e. shape, dimension, lacunar fill, orientation) were compared between Group specimens and between pre-and post-treatment specimens by combining patterns into comparable categories. Chondron density was determined both by quantifying cell populations per $mm^2$ in two-dimensional section images integrated at the tissue surface and by measuring inter-chondron distances. These calculations were designed to accommodate the problem of volumetric tissue ablation extraction observed with ablation devices, and therefore included counts and measurements spanning the Superficial and Transitional Zones, if present, at the tissue surface. Multiple range ANOVA analysis and two sided t-tests were performed for differences in depth of cartilage tissue necrosis, number of chondrocytes, and chondron population for each group.

Figure 22A:
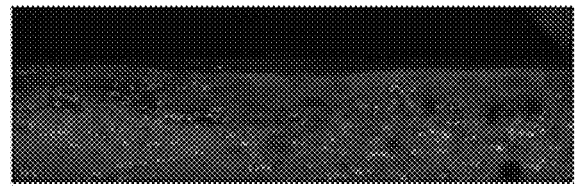
FIGS. 22A-C are comparison images which respectively illustrate a control sample, as well as samples which have been subjected to ablation and non-ablation treatments.
Figure 22B:
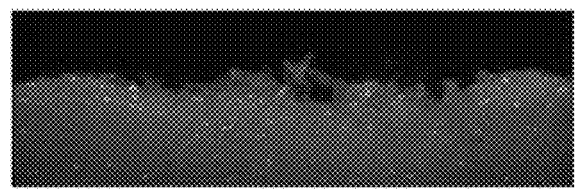
Figure 22C:
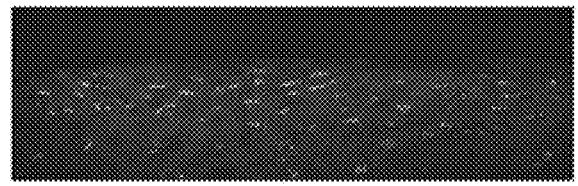

Six patients yielding six separate specimens were included for study, generating twenty-four osteochondral parts tested. Residual post-treatment tissue characteristics varied significantly between the treatment groups (FIG. 22).

Figure 23:
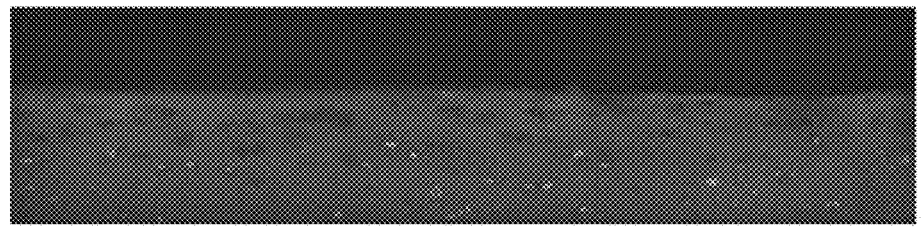
FIG. 23 is an image which illustrates an enlarged view of a control sample.

The Control specimens demonstrated tactile soft surfaces adjacent to areas of surface fibrillation consistent with gross visual inspection of the harvested tissues. Early lacunar emptying was evident mostly limited to the surface portion of the Superficial Zone (FIG. 23). Chondrocytes with a flattened chondron appearance typical of this zone remained present within the tactile soft surfaces with chondrocyte geographic patterns including singles, pairs, strings, and clusters as noted in FIG. 22. Live cells were abundantly present in chondrons in and around the tactile soft areas exhibiting lacunar emptying with evidence of chondrocyte depletion and some dead cell populations mostly at surface positions (<13% per mm2). Cell population densities within each specimen group remained constant as the sample parts of each group originated from the same specimen. Inter-specimen comparisons did not reveal significant differences in relative cell population density, chondrocyte geographic profile, chondron image character, or inter-chondron distance confirming similar lesion type included for study.

Figure 24:
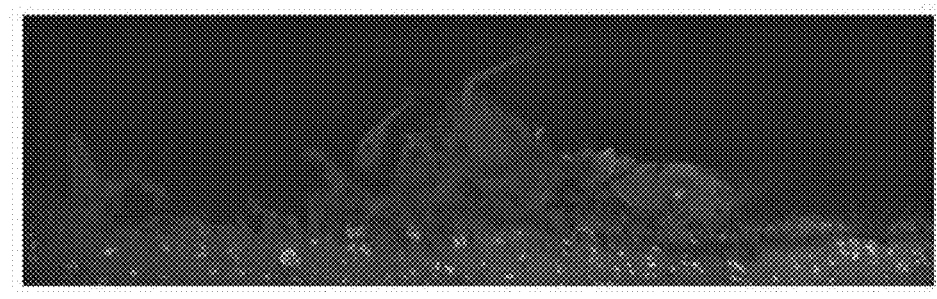
FIG. 24 is an image which illustrates an enlarged view of a sample which has been subjected to an ablation treatment.
Figure 25:
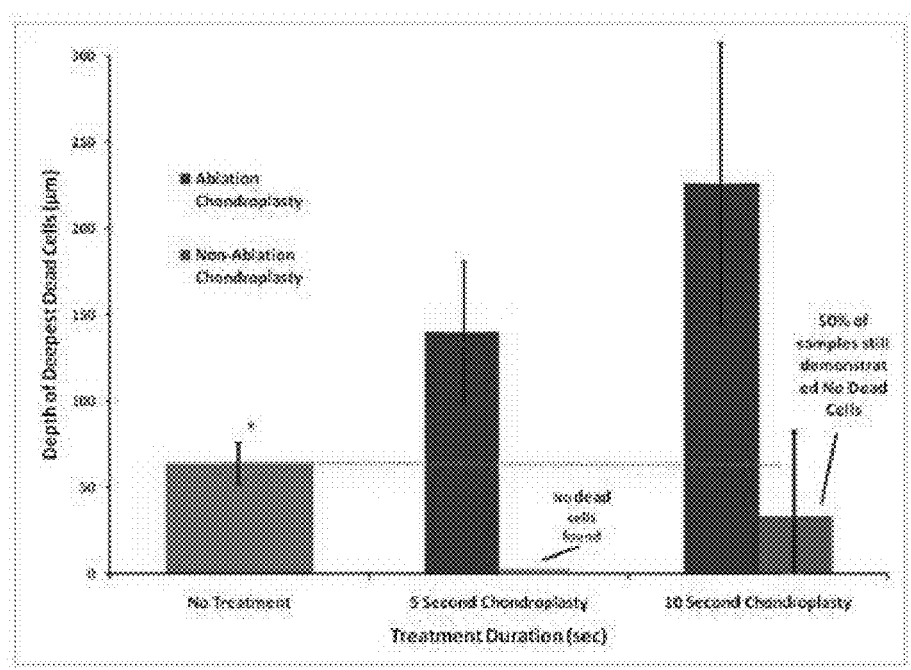
FIGS. 25 and 26 are graphs which respectively illustrate depth of necrosis and cell count comparisons between sample groups.
Figure 29:
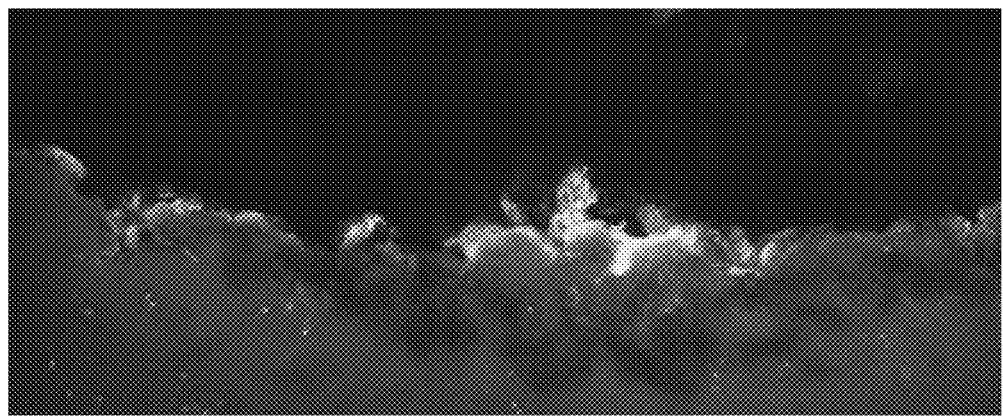
FIG. 29 is an image which illustrates ablation induced transitional zone alterations.
Figure 30:
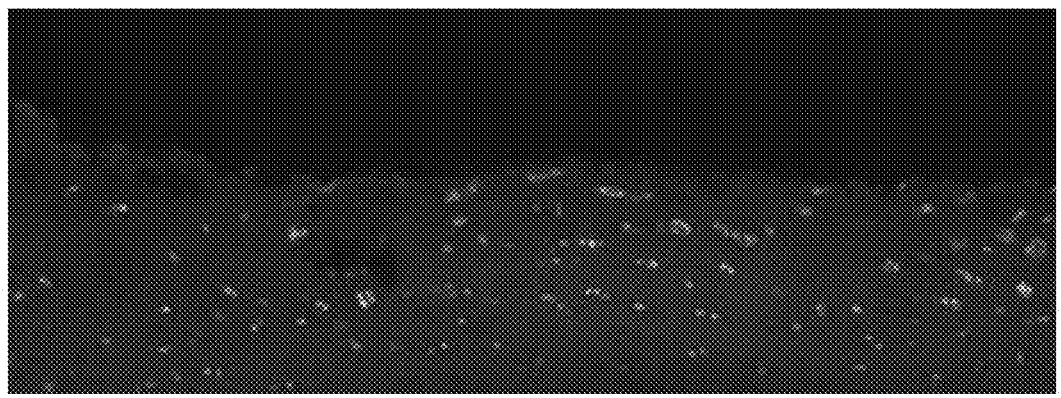
FIGS. 30 and 31 are images which respectively illustrate chondrocyte geographic profiles of samples after ablation and non-ablation treatments.

The Ablation specimens demonstrated large charred tissue segments, generalized gelatinization of tissue indicative of altered matrix properties, and loss of cartilage thickness above that of control throughout the treatment site. Tissue charring ranged from light-brownish color to near black or dark grey indicating severe char and tissue damage for the thermal ablation specimens. The gelatinized tissue was observed to have a semi-translucent appearance and much softer consistency than the surrounding cartilage in the plasma ablation specimens. Areas of tissue fragmentation indicating ablation extraction as is typically observed during standard electrocautery procedures were evident for both the thermal and plasma ablation specimens (FIG. 24). No treated specimens yielded either a visually or histologically smooth cartilage surface when compared to control. The tissue surface was replaced with a residual layer of necrotic and damaged tissue in all instances completely eliminating Superficial Zone characteristics due to volumetric tissue loss exceeding the level of disease pre-treatment (FIG. 22). Consequently, evaluations of Superficial Zone chondrons was not possible at the treatment site. Cellular density, geographic chondrocyte profile, chondron image character, and inter-chondron distance of the residual tissue under the necrotic layer depicted an altered and damaged Transitional Zone when compared to control specimens (FIG. 29). Dead cells were present in all specimens independent of chondrocyte geographic profile and occasionally intermixed with live cells to a varying degree (FIG. 30). As illustrated in FIG. 25, the mean post-treatment depth of necrosis was 140 fÊm (range 104 fÊm-199 fÊm) at 5 seconds and 226 fÊm at 10 seconds (range 140 fÊm-334 fÊm) through the residual Transitional Zone tissue (as distinct from necrosis through Superficial Zone tissue as this Zone had been volumetrically removed due to ablation tissue extraction).

Figure 31:
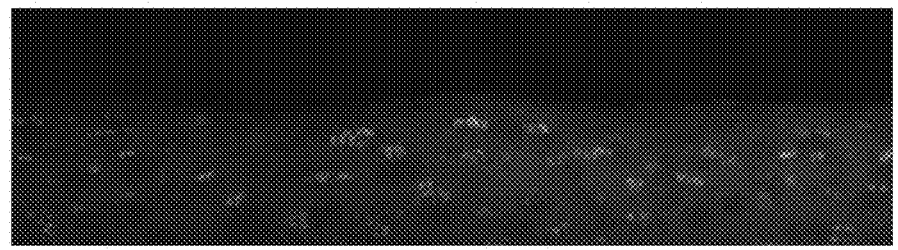

The Non-Ablation specimens demonstrated a smooth residual surface at the treatment site with no areas of charred, gelatinized, or color altered tissue and without bulk tissue loss. All specimens retained intact Superficial Zone characteristics in the residual tissue at the treatment site (FIG. 22). The chondrocyte geographic pattern and chondron image character of the retained Superficial Zone were not altered over control, with live chondrocytes persisting independent of their geographic profile (FIG. 31). Live cells were evident throughout the treatment site with chondrocytes residing closer to the surface and with a general decrease in inter-chondron measurement when compared to Control. This finding indicated a relative increase in surface-based cellularity post-treatment in the retained Superficial Zone of the treatment site. Areas of lacunar emptying and chondrocyte depletion evident in the Control specimens were generally not present. The Transitional Zone did not demonstrate altered cell density pattern, geographic chondrocyte profile, inter-chondron measurement, or evidence of cellular death. As illustrated in FIG. 25, no areas of necrosis or dead cells were observed at 5 seconds and only one treatment sample demonstrated any cell death at 10 seconds. In that sample, 3% of cells were found dead up to 67 fÊm deep limited to the Superficial Zone.

Figure 26:
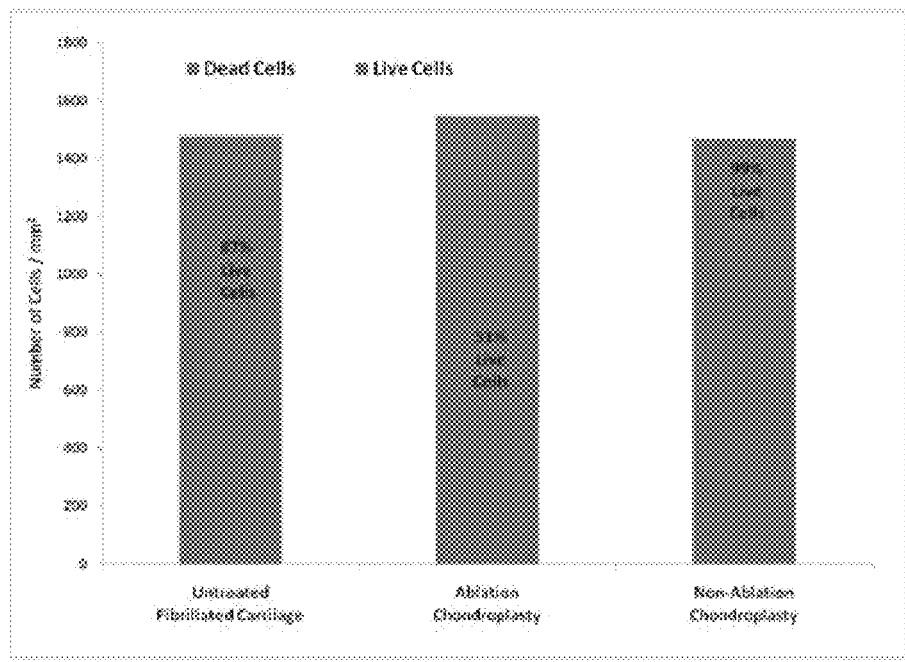
Figure 27:
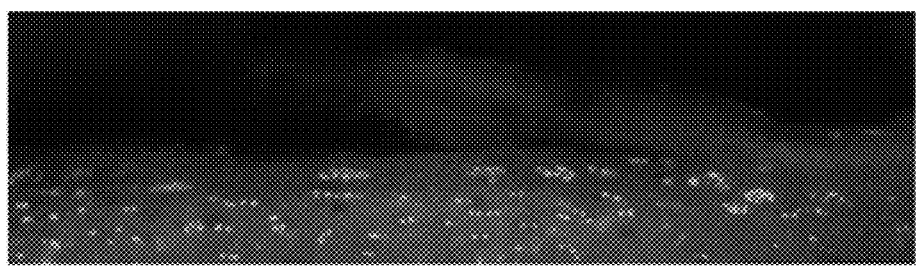
FIG. 27 is an enlarged image which illustrates a superficial zone cleavage plane.

FIG. 26 displays the comparison of cell counts for each treatment Group. Because of the volumetric tissue loss that occurred in the Ablation group, the comparison depicted is between the Control specimens with a Superficial Zone, the Ablation specimens without a Superficial Zone and an exposed Transitional Zone, and the Non-Ablation specimens with a retained Superficial Zone. The mean total cell number in Control sections was 1480 per mm2. Even though the Ablation method fully corrupted the Superficial Zone, the mean total cell number in the residual Transitional Zone tissue was 1546 per $mm^2$ (no statistical difference from control; $p<0.92$); yet, with a decreased live cell density of 36% over control ($p<0.02$) without necrosis preference relative to chondrocyte geographic profile within the chondrons. The Non-Ablation method which retained Superficial Zone characteristics demonstrated a mean total number of cells of 1468 per $mm^2$ (no statistical difference from control; $p<0.92$) with increased live cell density of 12% over control ($p<0.02$) independent of geographic chondrocyte profile within the chondrons. Cell count remained consistently proportional to chondron count throughout the sections. The decreased live chondron density of the Ablation group reflected primarily an increased cellular necrosis induced in the residual tissue commensurate with the volumetric ablation extraction of the tissue surfaces; whereas, the increased live chondron density of the Non-Ablation group reflected both a preferential extra-cellular matrix volume contraction whereby additional live cells were brought into the surface quantification area and a small cleavage plane surface removal of diseased Superficial Zone tissue (FIG. 27). Multiple range ANOVA analysis demonstrated a statistically significant difference between the depth of cartilage tissue necrosis ($p<0.004$) and percent chondrocyte death ($p<0.003$) between the Ablation group and the Non-Ablation group.

Thermal and plasma ablation treatments fully corrupt the Superficial Zone, both the matrix and cellular structures, with electrocautery-like tissue extraction, leaving an exposed and damaged Transitional Zone in place of the original tactile soft Superficial Zone. Since the control group exhibited significant live chondrocyte populations in the Superficial Zone, this example provides further evidence that thermal and plasma ablation treatments do not have a role in early intervention for articular cartilage lesions. Volumetric tissue loss can only contribute to articular cartilage lesion progression by converting a potentially salvageable lesion with Superficial Zone characteristics to one that may not be salvageable with an exposed and damaged Transitional Zone that can lead to accelerated wear. Unnecessarily induced volumetric tissue loss and cellular necrosis has been deemed inappropriate for an early intervention strategy; rather, the interest in treating early cartilage disease is that based upon tissue biology.

Further experiments were conducted with non-ablation radiofrequency energy designed to treat early articular cartilage lesions have verified no decrease in chondrocyte viability post-treatment when bulk tissue specimens were incubated for 96 hours.

The preceding examples can be repeated with similar success by substituting the generically or specifically described components and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An electrosurgical tool comprising:
a plenum comprising a plenum chamber and a knife blade, said plenum disposed at least partially around an active electrode, said plenum comprising one or more openings which permit fluid to enter said plenum chamber, and said plenum shielding tissue from said active electrode.

2. The tool of claim 1 comprising a plurality of said active electrodes.

3. The tool of claim 1 comprising a plurality of openings in said plenum.

4. The tool of claim 1 wherein said plenum exterior comprises a textured surface.

5. The tool of claim 4 wherein said textured surface comprises a roughened surface.

6. The tool of claim 1 wherein said plenum comprises a shape useful for a surgical procedure in addition to said knife blade.

7. The tool of claim 1 wherein said knife-blade is serrated.

8. The tool of claim 7 where said plenum comprises a plurality of elongated openings orientated along its primary axis.

9. The tool of claim 1 wherein said plenum comprises at least one elongated opening orientated along its primary axis.

10. The tool of claim 1 wherein the active electrode does not comprise any openings or flow-through channels.

11. A method for performing an electrosurgical procedure comprising:
providing an electrosurgical apparatus comprising active and return electrodes; and
disposing a plenum comprising a knife blade around the active electrode, the plenum further comprising one or more openings which permit entry of fluid while preventing anatomically-specific tissue structures from contacting the active electrode; and
manipulating the electrosurgical apparatus at a treatment site to perform the electrosurgical procedure.

12. The method of claim 11 wherein said anatomically-specific tissue comprises targeted tissue.

13. The method of claim 11 wherein said anatomically-specific tissue comprises intact tissue.

14. The method of claim 11 wherein the openings are disposed along a primary axis of the plenum.

15. The method of claim 11 wherein the plenum comprises a shape which is mechanically useful for a surgical procedure in addition to said knife blade.

16. The method of claim 11 wherein the plenum comprises a textured surface.

17. An electrosurgical tool comprising:
a plenum comprising a knife blade, said plenum disposed at least partially around an active electrode, said plenum comprising a plurality of openings which permit fluid to enter said plenum chamber.

* * * * *